United States Patent [19]
Gozes et al.

[11] Patent Number: 5,972,883
[45] Date of Patent: Oct. 26, 1999

[54] METHOD FOR THE TREATMENT OF NEURODEGENERATIVE DISEASES BY ADMINISTERING VIP, AN ANALOGUE, FRAGMENT OR A CONJUGATE THEREOF

[75] Inventors: Illana Gozes, Ramat Hasharon; Matityahu Fridkin, Rehovot, both of Israel

[73] Assignees: Yeda Research and Development Co. Ltd., Rehovot; Ramot University Authority for Applied Research and Industrial Development Ltd., Tel-Aviv, both of Israel

[21] Appl. No.: 08/413,708

[22] Filed: Mar. 30, 1995

Related U.S. Application Data

[63] Continuation-in-part of application No. 08/207,671, Mar. 9, 1994, abandoned.

[30] Foreign Application Priority Data

Mar. 16, 1993 [IL] Israel ..................................... 105061

[51] Int. Cl.$^6$ .................................................. A61K 38/00
[52] U.S. Cl. .......................................... 514/12; 530/324
[58] Field of Search .................... 514/12, 879; 530/324, 530/327, 328

[56] References Cited

U.S. PATENT DOCUMENTS

| | | | |
|---|---|---|---|
| 4,605,641 | 8/1986 | Bolin et al. | 514/12 |
| 5,147,855 | 9/1992 | Gozes et al. | 514/12 |

FOREIGN PATENT DOCUMENTS

| | | |
|---|---|---|
| 0354992 | 2/1990 | European Pat. Off. . |
| 9107947 | of 0000 | WIPO . |

OTHER PUBLICATIONS

Gordon et al. Neuroscience Letters. 199, 1–4, 1995.
Masliah et al. Experimental Neurology, 136, 107–122, 1995.
Masliah et al. Brian Research, 751, 307–314, 1997.
Oitzl et al. Brain Research, 752, 189–196, 1997.
Morris et al, Neurology,, 39, 1159–1165, 1989.
Raffaele et al, Psychopharmacol. 27, 315–319, 1991.
Gregoriadis, G. et al. 1993. T. Biotech. 11: 440–442.
Koutouzis, T.K. et al. 1994. Crit. Review Microbiol. 8(3): 125–162.
Brenneman, D.E. et al. 1985. Peptides 6:35–39.
Gozes, I et al. 1992. J. Clin. Invest. 90:810–814.
The Merck Index, 1976 pp. 223, 1136–1137. Merck & Co. Inc., Rahway, N.J.
Gozes et al., VIP: Molecular Biology and Neurobiological Function Molecular Neurobiology, vol. 3, pp. 201–236, 1989.
Hill et al, Vasoactive Intestinal Peptide Antagonist Retards the Development of Neonatal Behaviors in the Rat, Peptides, vol. 12, pp. 187–192, 1991.
Glowa et al, Learning Impairment Following Intracerebral Administration of the HIV Envelope protein gp120 or a VIP Antagonist, Brain Research, vol. 570, pp. 49–53, 1992.

Rossor et al, Reduced Cortical Choline Acetyltransferase Activity in Senile Dementia of Alzheimer type is not Accompanied by Changes in Vasoactive Intestinal Polypeptide, Brain Research, vol. 201, pp. 249–253, 1980.
Bouras et al, Neuropeptides in Alzheimer's Disease: A Review and Morphological Results, Prog. Neuro–Psychopharmacol & Biol. Psychiatry, vol. 10, pp. 271–286, 1986.
Sunderland et al, Reduced Cerebrospinal Fluid Dynorphin A1–8 in Alzheimer's Disease, Biol. Psychiatry, vol. 30, pp. 81–87, 1991.
Wikkelso et al, Neuropeptides in Cerebrospinal Fluid in Normal–Pressure Hydrocephalus and Dementia, Eur. Neurol, vol. 31, pp. 88–93, 1991.
Arai et al, Somatostatin and Vasoactive Intestinal Polypeptide in Postmortem Brains from Patients with Alzheimer–ype Dementia, Neurosci. Lett., vol. 52, pp. 73–78, 1984.
Brenneman et al, Nonneuronal Cells Mediate Neurotrophic Action of Vasoactive Intestinal Peptide, The Journal of Cell Biology, vol. 104, pp. 1603–1610, Jun. 1987.
McCarthy et al, Preparation of Separate Astroglial and Oligodendroglial Cell Cultures From Rat Cerebral Tissue, J. Cell Biology, vol. 85, pp. 890–902, Jun. 1980.
Evans et al, Regulation of Cyclic AMP Accumulation by Peptide Hormone Receptors in Immunocytochemically Defined Astroglial Cells, Journal of Neurochemistry, vol. 43, pp. 131–138, 1984.
Gozes et al, Vasoactive Intestinal Peptide Potentiates Sexual Behavior: Inhibition by Novel Antagonist, Endocrinology, vol. vol. 125, No. 6, pp. 2945–2949, 1989.
Gozes et al, An Antagonist to Vasoactive Intestinal Peptide Affects Cellular Functions in the Central Nervous System, The Journal of Pharmacology and Experimental Therapeutics, vol. 257, No. 3, pp. 959–966, 1991.
Gozes et al, A VIP Antagonist Distinguishes VIP Receptors on Spinal Cord Cells and Lymphocytes, Brain Research, vol. 540, pp. 319–321, 1991.

(List continued on next page.)

*Primary Examiner*—Paula K. Hutzell
*Assistant Examiner*—Lin Sun-Hoffman
*Attorney, Agent, or Firm*—Browdy and Neimark

[57] ABSTRACT

A method for the treatment of neurodegenerative diseases comprising administering to a patient in need of such treatment a therapeutically effective amount of a peptide compound selected from the group consisting of:
(i) vasoactive intestinal peptide (VIP);
(ii) analogues of vasoactive intestinal peptide (VIP) in which one or more amino acids has been replaced, added or deleted without substantially altering the biological properties of the parent peptide;
(iii) a conjugate being a peptide compound according to either of (i) and (ii) coupled to a lipophilic moiety;
(iv) a physiologically active fragment of (i), (ii) and (iii); and
(v) a functional derivative of any of (i), (ii), (iii) and (iv);
optionally in combination with a pharmaceutically acceptable carrier.

9 Claims, 11 Drawing Sheets

OTHER PUBLICATIONS

Fisher et al, (+)-cis-2-Methyl-spiro(1,3-oxathiolane-5,3') quinuclidine (AF102B): a new M1 agonist attenuates cognitive dysfunctions in AF64A-treated rats, Neurosci Letters, vol. 102, pp. 325-331, 1989.

Chiou, Systemic Delivery of Polypeptide Drugs Through Ocular Route, Annu. Rev. Pharmacol. Toxicol., vol. 31, pp. 457-467, 1991.

Forsythe et al, Slow Excitatory Postsynaptic Currents Medisted by N-Methyl- D-Aspartate Receptors on Cultured Mouse Central Neurones, Journal of Physiology, vol. 396, pp. 515-533, 1988.

Pike et al, Neurodegeneration Induced by B-Amyloid Peptides in vitro: The Role of Peptide Assembly State, The Journal of Neuroscience, vol. 13, No. 4, pp. 1676-1687, Apr. 1993.

Goldman et al, (1991), In "Principles of Newal Science", E.R. Kandel et al, eds., Elsevier Science Publishing Co., Inc., N.Y., pp. 974-983.

Stryer, (1988), "Biochemistry", W.H. Freeman and Co., N.Y., pp. 16-20 and 470-471.

"The Menck Index", M. Windholz et al, eds., (1976), Mench and Co., Inc., Rahway, N.J., pp. 223 and 1136-1137.

Gozes et al, (1994), Endocrinology, 134(5): 2121-2125.

Gozes et al, (1993), J. Molec. Neurosci., 4(3): 185-193.

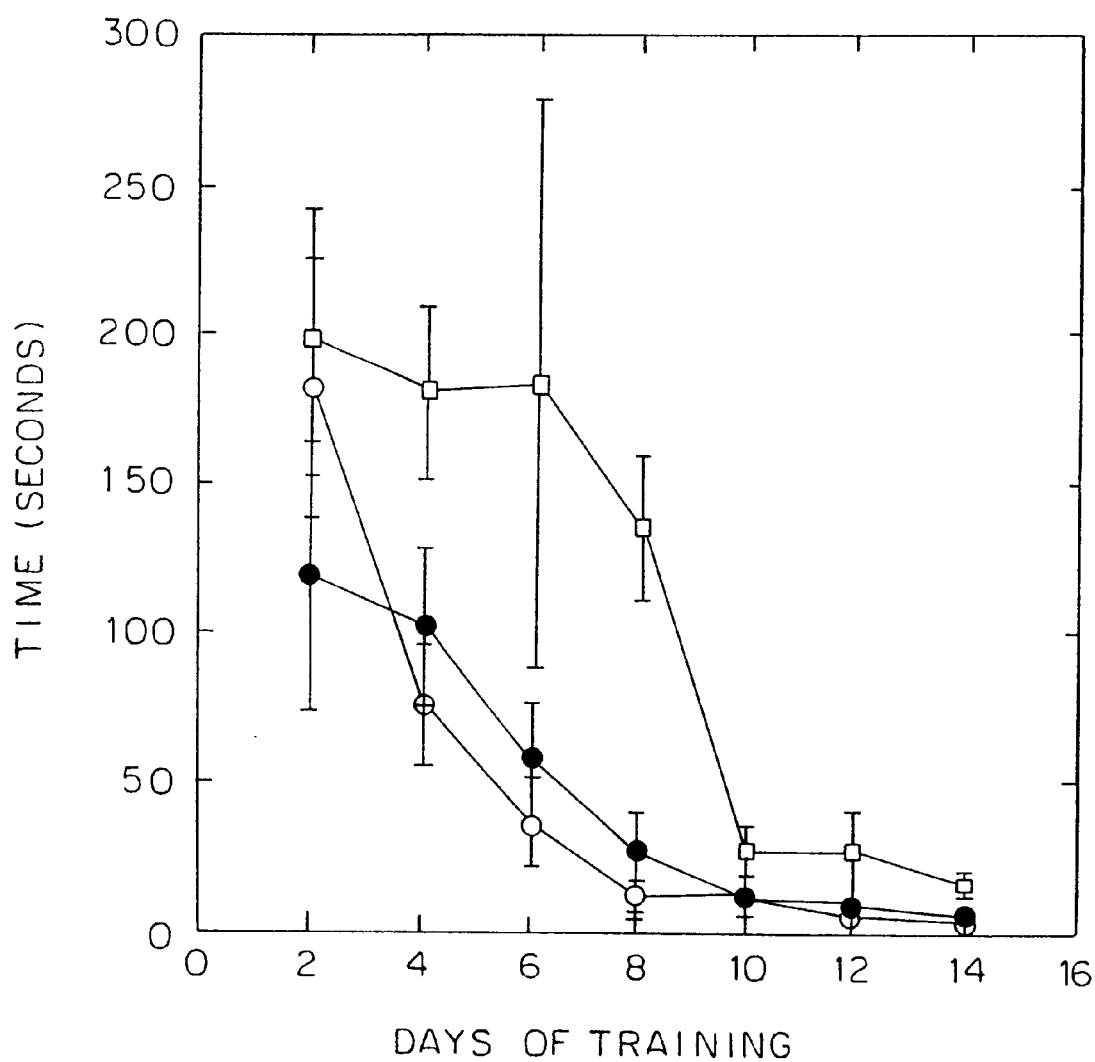
F I G. 10

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
        (A) LENGTH: 28 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1:

His Ser Asp Ala Val Phe Thr Asp Asn Tyr Thr Arg Leu Arg Lys Gln
1               5                   10                  15

Met Ala Val Lys Lys Tyr Leu Asn Ser Ile Leu Asn
            20                  25

(2) INFORMATION FOR SEQ ID NO:2:

(i) SEQUENCE CHARACTERISTICS:
        (A) LENGTH: 28 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

His Ser Asn Ala Xaa Phe Thr Asp Asn Tyr Thr Arg Leu Arg Lys Gln
1               5                   10                  15

Xaa Ala Xaa Lys Lys Tyr Leu Asn Ser Ile Leu Asn
            20                  25

(2) INFORMATION FOR SEQ ID NO:3:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

Ala Val Lys Lys Tyr Leu Asn Ser Ile Leu Asn
1               5                   10

(2) INFORMATION FOR SEQ ID NO:4:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

Ala Val Thr Thr Asp Asn Tyr Thr
1               5

(2) INFORMATION FOR SEQ ID NO:5:

```
        (i) SEQUENCE CHARACTERISTICS:
            (A) LENGTH: 14 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:5:

His Ser Asp Ala Val Phe Thr Asp Asn Tyr Thr Arg Leu Arg
1               5                  10

(2) INFORMATION FOR SEQ ID NO:6:

(i) SEQUENCE CHARACTERISTICS:
            (A) LENGTH: 13 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:6:

Lys Gln Met Ala Val Lys Lys Tyr Leu Ala Ala Val Leu
1               5                  10

(2) INFORMATION FOR SEQ ID NO:7:

(i) SEQUENCE CHARACTERISTICS:
            (A) LENGTH: 14 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:7:

His Ser Asp Gly Ile Phe Thr Asp Ser Tyr Ser Arg Tyr Arg
1               5                  10

(2) INFORMATION FOR SEQ ID NO:8:

(i) SEQUENCE CHARACTERISTICS:
            (A) LENGTH: 28 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION: 5, 17 and 19
            (D) OTHER INFORMATION: /note= "A residue of a natural or
                non-natural lipophilic amino acid"

(ix) FEATURE:
            (A) NAME/KEY: Peptide
            (B) LOCATION: 6
            (D) OTHER INFORMATION: /note= "Phe or Thr"

(ix) FEATURE:
            (A) NAME/KEY: Peptide
            (B) LOCATION: 24
            (D) OTHER INFORMATION: /note= "Asn or Ala"

(ix) FEATURE:
            (A) NAME/KEY: Peptide
            (B) LOCATION: 25
            (D) OTHER INFORMATION: /note= "Ser or Ala"

(ix) FEATURE:
            (A) NAME/KEY: Peptide
            (B) LOCATION: 25
```

-continued (D) OTHER INFORMATION: /note= "Ile or Val"

(xi) SEQUENCE DESCRIPTION: SEQ ID NO:8:

```
His Ser Asp Ala Xaa Xaa Thr Asp Asn Tyr Thr Arg Leu Arg Lys Gln
1               5                   10                  15

Xaa Ala Xaa Lys Lys Tyr Leu Xaa Xaa Xaa Leu Asn
            20                  25
```

METHOD FOR THE TREATMENT OF NEURODEGENERATIVE DISEASES BY ADMINISTERING VIP, AN ANALOGUE, FRAGMENT OR A CONJUGATE THEREOF

REFERENCE TO PRIOR APPLICATIONS

The present invention is a continuation-in-part of patent application Ser. No. 08/207,671 filed on Mar. 9, 1994, now abandoned the entire contents of which are hereby incorporated by reference.

FIELD OF THE INVENTION

The invention concerns a method for the treatment of neurodegenerative diseases, comprising administering to a patient an effective amount of vasoactive intestinal peptide (VIP), or of an analogue, a derivative, a fragment or of a conjugate thereof.

BACKGROUND OF THE INVENTION

Neurodegenerative diseases in which neuronal cells degenerate bring about a deterioration of cognitive functions. A variety of diseases and neurological deficiencies may bring about the degeneration of neuronal cells among them Alzheimer's disease, Huntington disease or chorea, hypoxia or ischemia caused by stroke, cell death caused by epilepsy, amyotrophic lateral sclerosis, mental retardation etc., as well as neurodegenerative changes resulting from aging.

Vasoactive intestinal peptide (VIP) is a 28 amino acid regulatory peptide which exhibits neurotransmitter and hormonal roles. VIP has a discrete distribution in the central nervous system (CNS), with highest levels in the cerebral cortex, hypothalamus, amygdala and corpus striatum. Accumulated evidence suggest the involvement of VIP in a multitude of neuronal functions among them: changes in membrane potential, modulation of muscarinic excitation, promotion of survival of electrically blocked neurons[1], maintenance of neural integrity[2], development of neonatal behavior in rats[3], rescue from neural death caused by HIV envelope protein. A VIP-receptor antagonist caused spatial learning impairment in rats which was attenuated by co-treatment with VIP, indicating a possible role for VIP in the process of learning[4].

There is conflicting evidence concerning the role of VIP in dementia in general and in Alzheimer's disease in particular. A large body of evidence suggests no such involvement. Rosor et at found no changes in VIP in cerebral cortex of brains obtained from patients suffering from senile dementia of the Alzheimer's type as compared to controls[5]. Other investigators found no variance in VIP measurement between Alzheimer's patients and controls[6,7,8], and no correlation was found between the degree of dementia and the concentration of VIP in the cerebrospinal fluid[9].

In contrast, a study of immunoreactivity of VIP in Alzheimer's and control brains showed a significant reduction of VIP immunoreactivity in the cerebral cortex especially in the insular and angulate cortex of Alzheimer's patients[10]. However, it has never been determined whether this reduction was the cause or rather the result of the Alzheimer's deterioration of the cerebral cortex.

SUMMARY OF THE INVENTION

According to the present invention it has been found that VIP, analogues, derivatives, fragments, and conjugates thereof caused recovery of learning activities in an animal model of Alzheimer.

Thus the present invention provides a method for the treatment of neurodegenerative diseases comprising administering to a patient in need of such treatment an effective amount of a peptide selected from the Croup consisting of:

(i) vasoactive intestinal peptide (VIP);

(ii) analogues of vasoactive intestinal peptide (VIP) in which one or more amino acids has been replaced, added or deleted without substantially altering the biological properties of the parent peptide;

(iii) a conjugate of a peptide according to either of (i) and (ii) coupled to a lipophilic moiety;

(iv) a physiologically active fragment of (i), (ii) and (iii); and (v) a functional derivative of any of (i), (ii), (iii) and (iv); optionally in combination with a pharmaceutically acceptable carrier.

In accordance with one embodiment of the invention, the peptide is VIP of the formula I:

```
            1                         7                              (I)
    H-His-Ser-Asp-Ala-Val-Phe-Thr-Asp-Asn-Tyr-Thr-Arg-Leu-Arg-    (SEQ ID NO:1)

16                                        28
    Lys-Gln-Met-Ala-Val-Lys-Lys-Tyr-Leu-Asn-Ser-Ile-Leu-Asn-NH₂
``` or a fragment thereof

In accordance with another embodiment of the invention the peptide is an analogue of VIP having the sequence of formula II:

```
            1                          7                             (II)
    H-His-Ser-Asp-Ala-X¹-Phe-Thr-Asp-Asn-Tyr-Thr-Arg-Leu-Arg-    (SEQ ID NO:2)

16                                        28
    Lys-Gln-X²-Ala-X³-Lys-Lys-Tyr-Leu-Asn-Ser-Ile-Leu-Asn-NH₂
``` wherein $X^1$, $X^2$ and $X^3$ may be the same or different and each is a residue of a natural or non-natural lipophilic amino acid, or a fragment of the peptide of formula II.

In yet another embodiment of the invention the peptide used in the method of the invention is a conjugate of a peptide of the sequence of Formula II, or a fragment thereof, with a lipophilic group having the formula III:

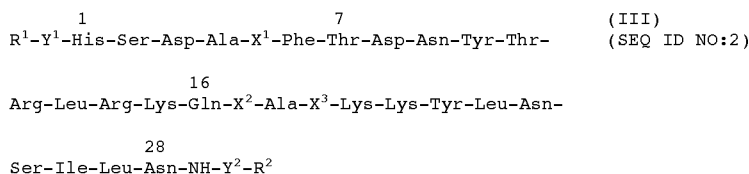

wherein

R$^1$ and R$^2$ may be the same or different and each is hydrogen, a saturated or unsaturated lipophilic group or a C$_1$–C$_4$ hydrocarbyl or carboxylic acyl, with the proviso that at least one of R$^1$ and R$^2$ is a lipophilic group;

Y$^1$ and Y$^2$ may be the same or different and each is —CH$_2$— or is a bond in case the associated R$^1$ or R$^2$ is hydrogen and Y$^1$ may further be —CO—; and X$^1$, X$^2$ and X$^3$ may be the same or different and each is a residue of a natural or non-natural lipophilic amino acid; or a physiologically active fragment or a functional derivative of said peptide of Formula III or of said physiologically active fragment.

X$^1$, X$^2$ and X$^3$ are preferably lipophilic amino acid residues represented by leucine, isoleucinc, norneucine, valine, tryptophan, phenylalanine, methionine, octahydroindole-2-carboxylic acid (oic), cyclohexylglycine (chg) and cyclopentylglycine (cpg).

The lipophilic moiety which is coupled to the VIP or the modified VIP of Formula II is preferably a saturated or unsaturated radical such as hydrocarbyl or carboxylic acyl having at least 5 carbon atoms. The lipophilic moiety can be attached at either or both of the N-terminus and C-terminus of the peptide molecule.

Particularly preferred peptides used in the method according to the invention are peptides of Formula III above in which X$^2$ is a norleucine residue, X$^1$ and X$^3$ are each valine, Y$^1$ is —CO— and R$^1$ is a C$_5$–C$_{17}$ alkyl with Y$^1$R$^1$ being, for example, stearoyl, lauroyl or caproyl, Y$^2$ is a bond and R$^2$ is hydrogen.

Functional derivatives as described herein are compounds in which at least one of the non-terminal amino acid residues bears a functional group in a side chain, while maintaining the biological properties of VIP as will be explained hereinbelow. Examples of functional groups are glycosides, ethers, esters with both carboxyl and hydroxyl groups, amides, etc.

Analogues of VIP as used herein are peptides in which one or more amino acids has been added, deleted or replaced by any means known in the art. The analogues of VIP which fall under the scope of the present invention are those which maintain the biological properties of native VIP is will be explained hereinbelow. Preferably, the Met at position 17 is replaced by Nle residue.

Physiologically active fragments as used herein are fragments of VIP, fragments of analogues of VIP, fragments of functional derivatives of VIP and fragments of conjugates of a lipophilic moiety with VIP or fragments of conjugates of a lipophilic moiety with analogues or functional derivatives.

The functional derivatives, physiologically active fragments, lipophilic conjugates and VIP analogues which fall under the scope of the invention are those which have the activity of protecting electrically blocked neurons from death, or of protecting untreated neurons in culture from naturally occurring death at concentrations which are essentially the same as or lower, as protective concentrations of native VIP, and/or which have the ability to enhance learning and memory acquisition when administered in vivo to animals in these concentrations.

The fragments of VIP or of its analogues or of conjugates thereof, are for example, fragments which have the sequence of amino acids 1 to 14 or 18 to 28 of VIP or fragments of the analogues of VIP which have one or more replacement in the following positions: position 6, preferably replacement by Thr; position 24, preferably replacement by Ala; position 25, preferably replacement by Ala; position 26, preferably replacement by Val.

Examples of conjugates of VIP fragments according to the invention are as follows:

St-VIP$_{18-28}$ (hereinafter "peptide 6") of the formula: St-Ala-Val-Lys-Lys-Tyr-Leu-Asn-Ser-Ile-Leu-Asn-amide (SEQ ID NO:3);

St-Thr$^6$-VIP$_{4-11}$ (hereinafter "peptide 5") of the formula: St-Ala-Val-Thr-Thr-Asp-Asn-Tyr-Thr-amide (SEQ ID NO:4);

St-VIP$_{1-14}$ (hereinafter "peptide 3") of the formula: St-His-Ser-Asp-Ala-Val-Phe-Thr-Asp-Asn-Tyr-Thr-Arg-Leu-Arg-amide (SEQ ID NO:5);

St-Ala$^{24}$,Ala$^{25}$,Val$^{26}$ VIP$_{15-27}$ (hereinafter "peptide 2") of the formula:

St-Lys-Gln-Met-Ala-Val-Lys-Lys-Tyr-Leu-Ala-Ala-Val-Leu-amide (SEQ ID NO:6);

modified VIP$_{1-14}$ fragment (hereinafter "peptide 1") of the formula: St-His-Ser-Asp-Gly-Ee-Phe-Thr-Asp-Ser-Tyr-Ser-Arg-Tyr-Arg-amide (SEQ ID NO:7).

The peptide chains of the peptides used in the method according to the invention are best prepared by solid phase synthesists[11,12] as known per se and once these chains are assembled a terminal group R$^1$Y$^1$-and/or R$^2$Y$^2$-that is other than hydrogen, is attached thereto.

When Y$^1$ is a carbonyl group, i.e. compounds with terminal R$^1$CO—, the R$^1$CO— group may be introduced by conventional acylation procedures.

In the preparation of compounds for use in the method according to the invention in which Y$^1$ is —CH$_2$—, i.e. compounds with terminal R$^1$—CH$_2$—, the R$^1$—CH$_2$-radical may be introduced by first coupling with an aldehyde R$^1$CH═O and then reducing the resulting R$^1$—CH═N— grouping by methods known per se. Compounds with terminal R$^2$—CH$_2$— are obtained by cleaving the peptide with an amine of the formula R$^2$—CH—NH$_2$.

The peptides may be administered with carriers. The optional carriers of the pharmaceutical compositions for use in the method of the invention can be any vehicle for parenteral, oral, aerosol, nasal or ocular administration of drugs acting on the central nervous system. It is preferable to administer a composition according to the invention through the nose, which enables the penetration of the aerosol composition to the CNS through the olfactory nerve (WO 91107947) or via the ocular route (Chiou, G. C. Y., (1991) *Ann. Rev. Pharmacol. Toxical,* 31:457–67) or by any other suitable method of administration as described in W. M. Pardridge, *Peptide Drug Delivery,* Raven Press, N.Y., 1991. The pharmaceutical compositions may be also directly targeted to the brain by an intercerebroventricular pump.

The term "treatment" used hereinafter does not necessarily mean that the neurodegenerative disease is completely eliminated, but rather that the cognitive facilities damaged by the disease are improved.

The term "neurodegenerative disease" is used hereinafter to denote conditions which result in degeneration of neural cells in the brain which bring about deterioration of cognitive function. Such degeneration of neural cells may be caused by Alzheimer's disease; Huntington disease or chorea; by pathological conditions caused by temporary lack of blood or oxygen supply to the brain, brought about by strock; by epileptic seizures; due to chronical conditions such as amyotrophic lateral sclerosis, mental retardation; as well as due to normal chances caused by aging.

The following examples illustrate the various aspects of the invention it being understood that the invention is not limited thereto.

The following terms used hereinafter have the following connotations:

VIP—Vasoactive intestinal peptide;
St-VIP—Stearoyl-VIP;
$Nle^{17}$-VIP—Norleucine$^{17}$-VIP;
St-$Nle^{17}$-VIP—Stearoyl-noricucine$^{17}$-VIP.

BRIEF DESCRIPTION OF DRAWINGS

For better understanding the invention will be described hereinafter, by way of example only, with reference to the annexed drawings in which:

FIG. 10 shows leaning and memory studies in control animals (○), animals injected I.C.V. with cholinergic blockers (□) and animals injected I.C.V. with cholinergic blockers and St-$Nle^{17}$-VIP (●);

Figure 1:
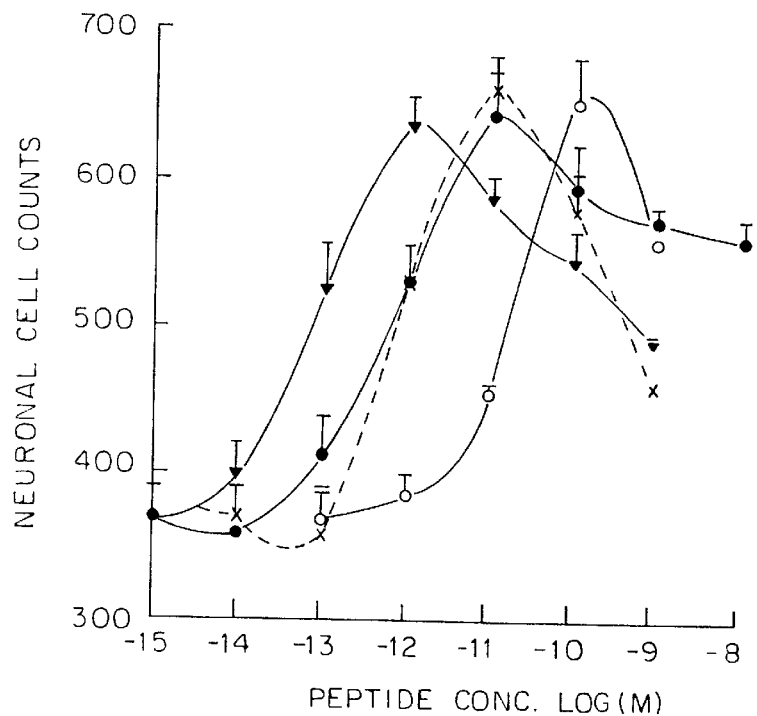
FIG. 1 shows the effect of varying concentration of VIP (○), St-$Nle^{17}$-VIP (▼), $Nle^{17}$-VIP (■) and St-VIP (●) on the survival of electrically blocked neurons.

The following non-limiting examples illustrate the invention.

EXAMPLE 1

Synthesis of Stearoyl-$Nle^{17}$-VIP

Synthesis of St-$Nle^{17}$-VIP was performed as follows:

The peptide chain was assembled manually in a mechanical shaker according to the general principles of the solid-phase methodology of Merrifield on a 4-(2',4'-dimethoxyphenyl-aminomethyl)-phenoxy resin, purchased from Nova, Switzerland. All solvents: methylene chloride ($CH_2Cl_2$), N-methylpyrrolidone (NMP), and dimethyl formamide (DMF) were analytical products of Merck, Germany. Trifluoroacetic acid (TFA), diisopropylethyiamine (DIEA) and N,N'-dicyclohexylcarbodiimide (ICC) were purchased from Aldrich, U.S.A. 1-Hydroxybenzotriazole (HOBT) was obtained from Nova, Switzerland. All protected amino acid derivatives (FMOC-AA) were of the L-configuration and were obtained from Bachem, Switzerland. $N^α$-amino acid functions were protected throughout the synthesis by the fluorenylmethoxycarlbonyl (FMOC) group. Side chain functions were protected as follows: Ser, Asp, Thr with t-butyl; Lys with t-butyloxycarbonyl; His with benzyloxymethyl (BOM); and Arg with methoxytrimethylphenylsulfonyl (Mtr).

The synthesis was initiated by removal of the FMOC-group, from the commercial polymer: 4-(2',4'-dimethoxyphenyl-FMOC-aminoethyl)phenoxy resin (0.47 mmol of amino group/g), according to steps 1 and 2 (see protocol). 10 g of polymer, contained in 2 reaction vessels, were employed. The volume of solvents used was 20–25 ml in each vessel. Assembly of the peptide chain was initiated by coupling FMOC-Asn (1.42 g, 4 mmol) to the resin (5 g) using DCC (0.84 g, 4 mmo)) and HOBT (0.55 g, 4 mmol) as agents. The coupling was repeated. Loading (0.39 mmol/g) was determined by amino acid analysis. Unreacted residual amino groups on the polymer were capped by reacting with acetic anhydride (10%) and diisopropylethylamine (5%) in $CH_2Cl_2$. The peptide chain assembly was started from the FMOC-Asn- resin, following the protocol outlined in Table 2.

TABLE 2

| Solid Phase Peptide Synthesis | | |
| --- | --- | --- |
| Step | Reagents | min. |
| 1 | 10% piperidine/DMF | 5 |
| 2 | 20% piperidine/DMF | 15 |
| 3 | DMF | 2 |
| 4 | DMF | 2 |
| 5 | DMF | 2 |
| 6 | $CH_2Cl_2$ | 2 |
| 7 | $CH_2Cl_2$ | 2 |
| 8 | NMP | 2 |
| 9 | Ninhydrin test | |
| 10 | FMOC-amino acid/HOBT/DCC (molar ratio 1:1:1 in NMP preactivation) | 120 |
| 11 | DMF | 2 × 2 |
| 12 | $CH_2Cl_2$ | 2 |
| 13 | $CH_2Cl_2$ | 2 |
| 14 | $CH_2Cl_2$ | 2 |
| 15 | Ninhydrin test | |
| 16 | 10% $Ac_2O$ + 5% DIEA in $CH_2Cl_2$ | 3 |

TABLE 2-continued

Solid Phase Peptide Synthesis

| Step | Reagents | min. |
|---|---|---|
| 17 | 10% $Ac_2O$ in $CH_2Cl_2$ | 5 |
| 18 | $CH_2Cl_2$ | 2 |
| 19 | $CH_2Cl_2$ | 2 |
| 20 | $CH_2Cl_2$ | 2 |
| 21 | DMF | 2 |

Solvents for all washings and reactions were measured to volumes of 10 ml/g resin, except for coupling (step 10) when volumes of about 5 ml/g resin were employed. All couplings were performed using HOBT active esters of FMOC-amino acid derivatives, prepared by DCC prior to each coupling step. A molar ratio of 2:1 of FMOC-amino acid 1-hydroxybenzotriazole ester (FMOC-AA-OBT) and α-amino group of growing peptide chain, respectively, was employed for couplings. Coupling reactions were monitored by boiling a few mg (about 3) of polymer in a solution of ninhydrin in pyridine-water for 2 min. Coupling of FMOC-amino acids was repeated twice or more to ensure complete reaction. In the second, and when necessary other, couplings, half of the amount of FMOCAA-OBT was used. Proceeding steps, aired at addition of the next amino acid were initiated only after a negative ninhydrin test (step 15; see protocol). As a rule, after completion of each coupling step, residual amine groups were capped by treating the resin with acetic anhydride (10%) and diisopropylethylamine (5%) in methylene chloride.

Following completion of the peptide chain assembly, the FMOC protecting group of His was removed, as usual, by piperidine in DMF and the newly free α-amino croup was coupled (in each reaction vessel) to stearic acid (1.14 g, 4 mmol) using DCC (0.84 g, 4 mmol) and HOBT (0.54 g, 4 mmol) as reagents. The reaction proceeded for 120 min and was repeated twice. The resin containing the fully assembled peptide-chain was washed with $CH_2Cl_2$ according to protocol, and then dried under vacuum overnight, over $P_2O_5$. Deblocking of protecting groups and cleavage of the peptide from resin was achieved as follows: 1 g of dried resin was placed in a 100 cc flask to which thioanisole (2 ml) and ethanedithiol (2 ml) were added. The mixture was cooled to 4° C. in an ice bath and 20 ml of trifluoroacetic acid added, and 5 min later trifluoromethanesulfonic acid (2 ml) was also added. The mixture was gently stirred at room temperature for 50 min.

The reaction mixture was then cooled to 4° C. and poured into 500 ml of dry ether. After stirring for 60 min at 4° C., the solid material (resin and peptide) was filtered on a scinter funnel, washed with dry ether, dried and then extracted with 50% aqueous acetic acid (100 ml). The solution obtained, containing the peptide, was concentrated in high vacuum and the residue (about 15 ml) was directly loaded on a Sephadex G25 column (45×6 cm), The column was eluted with 0.1N acetic acid at a flow rate of 45 ml/l hr. Elution was monitored at 274 nm. Lyophilization of the aqueous solution, containing the desired fraction, yielded the peptide free of the aromatic additives added as scavengers at the acidolytic cleavage step. Yield was about 400 mg of a white powder.

The material showed the required amino acid content and ratio as revealed by amino acid analysis following exhaustive acid hydrolysis.

Further purification by high performance liquid chromatography (HPLC) was carried out on the Sephadex-fractionated products. It can be performed, however, on the crude peptide. Purifications were achieved on Merck RP-8 column (7 μM, 250×25 mm column). The peptide was applied in 35% acetonitrile in water and eluted with a linear gradient established between 35% acetonitrile and 0.1% TFA in water and 0.1% TFA in 75% acetonitrile in water at a flow rate of 10 ml/min. Fractions were collected and cuts made after inspection by analytical HPLC. Derived fractions were pooled and lyophilized. Yield of the pure peptide was 30–35%.

EXAMPLE 2

Preparation of $R^1$—$CH_2$—$Nle^{17}$-VIP Derivatives

The peptide chain is assembled on the polymeric support, methyl benzhydryl amine resin (MBHA) (Nova, Switzerland), (containing 0.39 mmol Asn/1 gr) as described in Example 1. After incorporation of the last amino acid residue (histidine) the N-α-protecting group (t-Boc) is removed by TFA, the polymer is treated with DIEA, washed and ninhydrin tested. The polymer is then suspended in ethyl alcohol. (1 gr/10 ml) and the corresponding aldehyde R'—CH=O is added (3–4 equivalents of aldehyde to 1 equivalent of free N-terminal amino group) and the mixture is gently agitated overnight at room temperature. The polymer is filtered, washed with ethanol (3×10 ml), resuspended in ethanol and $NaBH_4$ (3–4 equivalents of reducing agent to 1 equivalent of Schiff base; R'—CH=N—His-) and the mixture is gently agitated for 2 hr at room temperature. Alternatively, $NaBH_3CN$ (3–4 equivalents to 1 equivalent of Schiff base) can be employed (in the presence of 0.1–0.2 ml of acetic acid). Condensation and reduction reactions can also be performed in other organic solvents, such as DMF or NMP. Following completion of reduction, the polymer is filtered, washed and dried, and treated with HF as described for stearoyl-$Nle^{17}$-VIP. The crude product is purified in the same manner as described in Example 1, to afford the desired final products.

EXAMPLE 3

Preparation of $R^1$—$Y^1$—NH—$Nle^{17}$-VIP-NH—$R^2$

The first amino acid, Boc-Asn, was attached to 1% crosslinked chloromethylated polystyrene (Chemalog, South Plainfield, N.J., U.S.A.) as follows: triethylamine (4.75 mmol; 0.66 ml) was added to the amino acid derivative (5 mmole; 1.16 gr) in absolute ethanol (35 ml), and the mixture was allowed to stand for 5 min at room temperature. The polymer (5 gr) was then added and the mixture was gently refluxed for 60 h at 78° C. Alternatively, 5 mmol of Boc-Asn was dissolved in a mixture of EtOH (12 ml) and water (3 ml), and the pH adjusted to 7.5 with a 20% aqueous solution of $Cs_2CO_3$. The solution was flash evaporated three times with benzene and the residue dried over $P_2O_5$ in a dessicator for 5 h. DMF (30 ml) was then added to dissolve the material, followed by 5 gr of polymer and the mixture was stirred for 36 h at 50° C. Loading (0.4 mmol/gr) was determined by amino acid analysis.

Peptide chain assembly was performed as described in Example 1 of EP 540969. However, Boc-Asp (β-cyclohexyl ester) was used instead of Boc-Asp (β-benzyl ester). The cyclohexyl group is stable toward aminolysis. On completion of the desired peptide chain assembly, the polymer is washed and dried as above. The product is then suspended in absolute ethanol, or a 1:1 v/v mixture of EtOH, and DMF (1 gr/10 ml) and the corresponding amine (R"-NH$_2$; 20 mmol) is then added and the mixture is gently stirred at room temperature for 48 h. TLC, using the solvent system N-butanol:acetic acid:H$_2$O;pyridine (15:3:12:10 v/v), revealed the appearance of a product which was detached from the polymeric support. The polymer was extracted with ethanol (3×10 ml), DMF (3×10 ml) and the solvents were evaporated in high vacuum and the oily, semi-solid, residue was then treated, as above, with HF to remove side-chain protecting groups. The crude products were purified in the same manner and comparative yields as described for stearoyl-Nle$^{17}$-VIP, to afford the desired final products.

EXAMPLE 4

Peptide Synthesis Via Automatic Procedure

Syntheses of St-Nle$^{17}$-VIP, caproyl-Nle$^{17}$-VIP and lauroylNlel$^7$-VIP, as well as all other lipophilic-VIP and modified-VIP fragments, were also achieved by automatic procedure employing an ABIMED AMS 422 synthesizer (ABIMED, Lancgenfeld, Germany) using the commercially available protocols via the Finoc-strategy, All protected amino acid derivatives were as previously outlined for the manual Fmoc-procedure with one exception, i.e. Fmoc-Arg (PMC), (PMC=2, 2, 5, 7, 8-pentamethylchroman-6-sulphonyl), replaced Fmoc-Arg(Mtr). PyBOP, i.e. benzotriazoIyl-N-oxy-tris(dimethylamino)phosphonium hexafluoro-phosphate, was used as a coupling agent. Peptide chains were assembled as in Example 1, on a 4-([2',4'-dimethoxyphenyl]-Fmoc-amino-ethyl)phenoxy resin (Rink Amide Resin, Nova, Switzerland).

Final cleavage of the peptide chain from the resin along with side chain deprotection was achieved as follows: cleavage mixture: 90% TFA, 5% water, 5% triethylsilane. The resin, 100 mg, loaded with peptide was incubated for 30 min. with a 3 ml cleavage mixture inside the reaction column used for solid phase synthesis. After 30 min, the reaction mixture was separated from the cleaved resin and cleavage continued for an additional 3 hrs. The cleaved peptide was precipitated with ice cold tert-butylmethyl ether and centrifuged (4° C., 2000 rpm). The solution was decanted and the pellet was dissolved in water and frozen for lyophilization to yield a white powder. Purification of the crude peptides was performed as described above. Yields were 30–45%.

The modified fragments, i.e., peptides 1, 2, 3, 5 and 6 were purified by HPLC on Merck RP-8 column (7 $\mu$M, 250×25 mm) by a linear gradient established between 0.1/TFA in water (solvent A) and 0.1% TFA in 75% acetonitrile in water (solvent B) at a flow rate of 10 ml/min. Analysis of products was carried out by analytical Merck, RP-8 column (12.5×4 mm) using linear gradient: t=0 min, 50% A and 50% B; t=40 min 0% A and 100% B at flow rate of 1 ml/min, revealed the following retention times: peptide 1=21.7 min; peptide 3=21.8 min; peptide 5=23.6 min; peptide 2=24.0 min; peptide 6=26.5 min.

EXAMPLE 5

Biological Tests—Effect of VIP And VIP Analogues And Conjugates Thereof On the Survival of Electrically Blocked Cells Method (a) Mouse spinal cord neurons obtained from 12 day old embryos were cultured as described previously$^{(15)}$. The neurons were plated in 10% horse serum 10% fetal calf serum in minimum essential medium eagle (MEM). Medium was changed to 5% horse serum supplemented with nutrients$^{(15)}$ after a day. Nine days after plating, cultures were given a complete change of medium. All cultures were treated with 1 $\mu$M tetrodotoxin (TTX), which is a blocker of electrical activity in neurons, and then divided into four groups. Group 1 was treated with varying concentrations of VIP, group 2 was treated with varying concentrations of Nle$^{17}$-VIP, group 3 was treated with varying concentrations of St-VIP, and group 4 was treated with varying amounts of St-Nle$^{17}$-VIP. The cultures were treated with VIP or its analogues from day 9 to day 14 and then fixed for immunocytochemistry for neuron specific enolase (NSE), which is a marker of viable neurons. The cells were counted on 100 fields with total area of 50 mm$^2$ in a blind test, without knowledge of treatment.

Results (b) The results are shown in FIG. 1. As can be seen in FIG. 1, all active agents tested protected electrically blocked cells from death to a certain degree, St-VIP and Nle$^{17}$-VIP being about 10 fold more potent than native VIP and St-Nle$^{17}$-VIP being about 100 fold more potent than native VIP. Both active agents with the hydrophobic moiety (St-VIP and St-Nle$^{17}$-VIP) caused also broadening of the peak of active concentrations.

The above results signify that the active agents of the invention are very potent protectors of electrically blocked neurons and thus can serve to decrease neuronal death and subsequent failing in cognitive abilities.

EXAMPLE 6

Biological Test—Effects of Peptides 1, 2 And 6 on Survival of Neurons

Method (a) Cerebral cortical cultures were prepared by a slight modification of the techniques described by Forsythe and Westbrook, (a. Physiol. Lond. 396:515 (1988)), in which cerebral cortex was used instead of hippocampus and new-born rats were utilized instead of E16 mice. After nine days growth in vitro, the cultures were given a complete change of medium and treated with serial dilutions of either peptide 1, 2 or 6 in order to determine whether these peptides were effective in protecting neurons from naturally occurring death. Cerebral cortical cells were counted as above, however, only 40 fields per plate were counted comprising an area of 20 mm$^2$.

Figure 2:
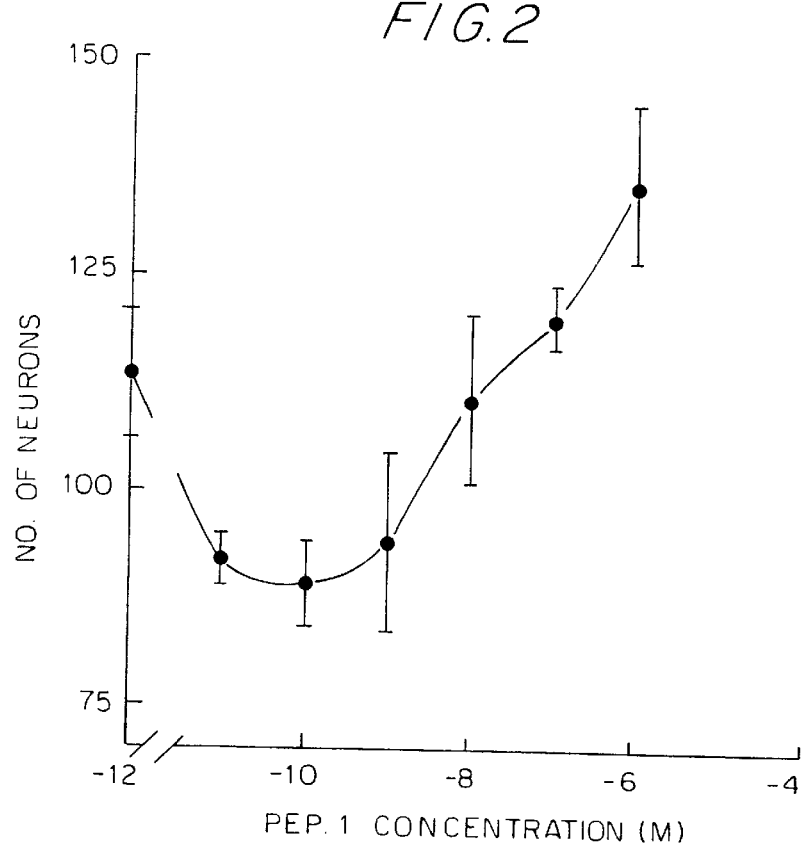
FIG. 2 shows the effect of various concentration of peptide 1 on the survival of untreated neurons.
Figure 3:
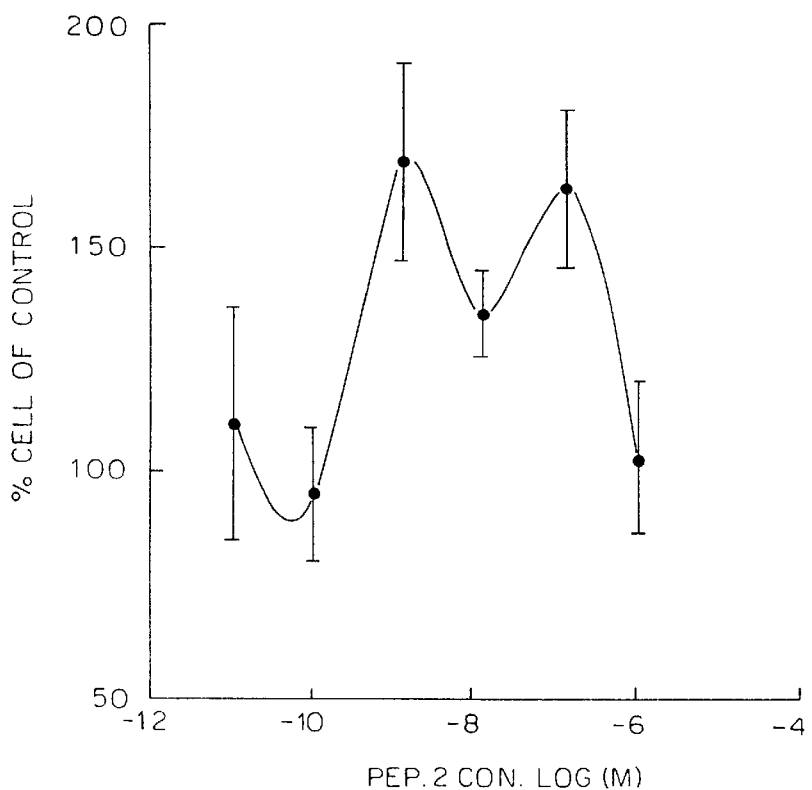
FIG. 3 shows the effect of various concentrations of peptide 2 on the survival of untreated neurons.
Figure 4:
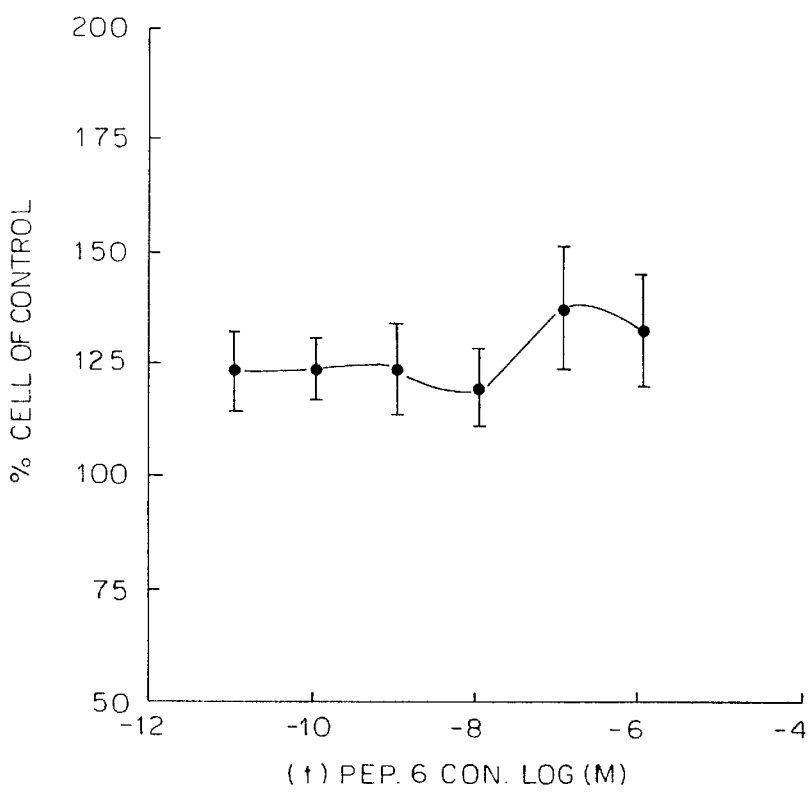
FIG. 4 shows the effect of various concentrations of peptide 6 on the survival of untreated neurons.

Results (b) As can be seen in FIG. 2, peptide 1 was able to protect cells from naturally occurring death at concentrations above 10$^{-8}$ M (the number of cells at 10$^{-12}$ M serves as control). FIG. 3 shows that peptide 2 was able to protect cells from death at concentrations above 10$^{-9}$ M declining at 10$^{-6}$ M and FIG. 4 shows that peptide 6 was able to protect cells from natural occurring death at all concentrations tested beginning at 10$^{-11}$ M.

The above results indicate that the active agents of the invention, can protect neurons not only from death caused by electric blockage but also from naturally occurring death.

EXAMPLE 7

Biological Tests—Effects of Peptide 5 And Peptide 3 on Survival of Neurons Treated With a VIP Antagonist, And Effect of Reptide 5 on Untreated Neurons Method (a) Cells were prepared as described in Example 6. After nine days growth in vitro, the cultures were given a complete change of medium and treated with serial dilutions of peptide 5 or of peptide 3 in the presence and in the absence of $10^{-8}$ M of a VIP antagonist described in detail in U.S. Pat. No. 5,217,953. One treatment was given at the beginning of a five day test period. Cell counts were performed on 100 fields, with a total area of 50 mm$^2$. Neurons were counted without knowledge of treatment.

Figure 5A:
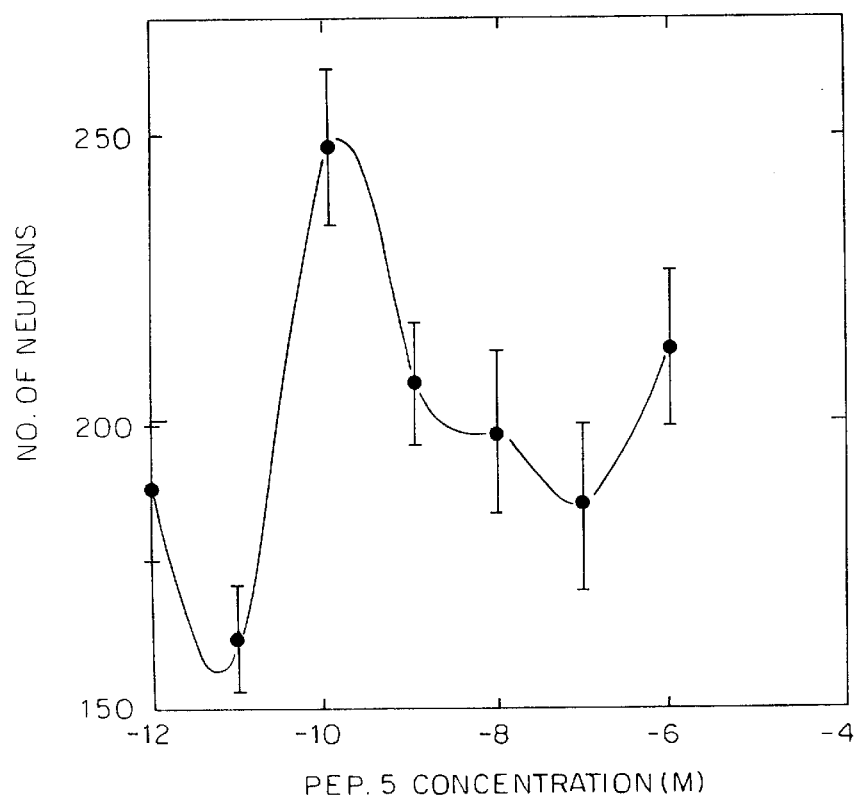
FIGS. 5 A–B show the effect of various concentrations of peptide 5 on the survival of neurons treated with a VIP antagonist FIG. 5A) and untreated neurons (FIG. 5B)
Figure 5B:
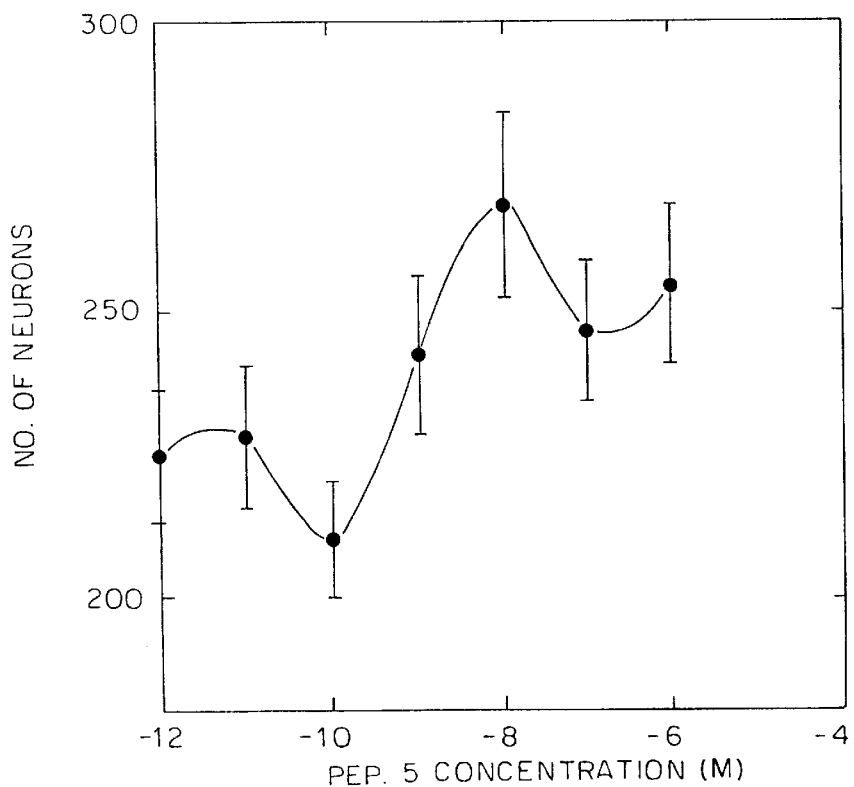

Results (a) As can be seen in FIG. 5, peptide 5 is a VIP agonist, stimulating neuronal survival in the presence (FIG. 5A) and in the absence (FIG. 5B) of the VIP antagonist indicating that peptide 5 can protect neurons from naturally occurring death. It should be noted that in the presence of the VIP antagonist, the maximal activity is obtained at $10^{-10}$ M, while in absence of the VIP antagonist the maximal activity is seen at $10^{-8}$ M, suggesting that the VIP antagonist renders the system more sensitive and enables peptide 5 to exert its protective effects at lower concentrations.

Figure 6:
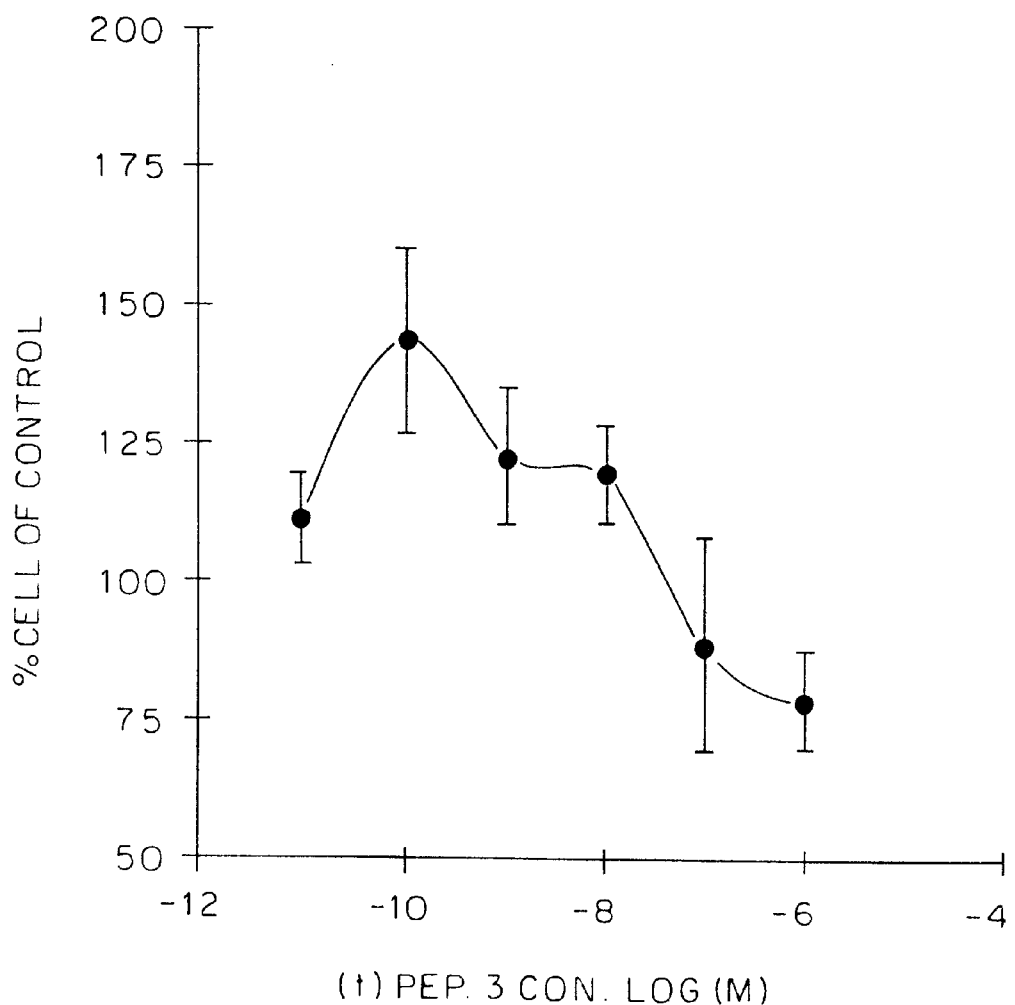
FIG. 6 shows the effect of various concentrations of peptide 3 on the survival of neurons treated with a VIP-antagonist.

FIG. 6 shows that peptide 3 was also able to protect neurons from death caused by the VIP antagonist showing peak activity at $10^{-10}$ M. Furthermore, the fact that in the presence of $10^{-10}$–$10^{-3}$ M of peptide 3 the cell counts were higher than those of control untreated cells, indicates that peptide 3 was able to protect cells from naturally occurring death.

EXAMPLE 8

Biological Tests—Effects of St-Nle$^{17}$-VIP, Peptide 3 And a Combination of Peptide 3+Peptide 6 on Survival of Neurons Treated With Fragment 25–35 of β-amyloid Peptide Method β-Amyloid peptide is known to be involved in Alzheimer's disease and is a toxic substance to neurons grown in culture (Pike et at, *J. of Neurosci.*, 13(4), 1676–1687 (1993); Yankner et al., *Science*, 250, 279–282 (1990)); Pike et al., *Soc. Areurosci. Abs.*, 20, 1247 (1994); Terzi, et at, *Biochemistry*, 33, 7434–7441, (1994)). Neurons from rat cerebral cortex, prepared as described above were treated with 25 μM of β-amyloid peptide fragment comprising amino acids in positions 25 to 35 mentioned in the above publication. The β-amyloid peptide fragment was dissolved in water and preincubated at 37° C. for 48 h in 10% CO$_2$. St-Nle$^{17}$-VIP, peptide 3 or a combination of 50% peptide 3 and 50% peptide 6 (10 μl/1 ml medium) were added to the culture plates at varying concentrations together with the β-amyloid peptide fragment. The peptides were initially dissolved in DMSO to give a concentration of $10^{-3}$ M and all further dilutions were performed in saline. Cells were then incubated for 5 days, stained with antibodies against neuron specific enolase and living neurons were counted as described above.

Results

Figure 7:
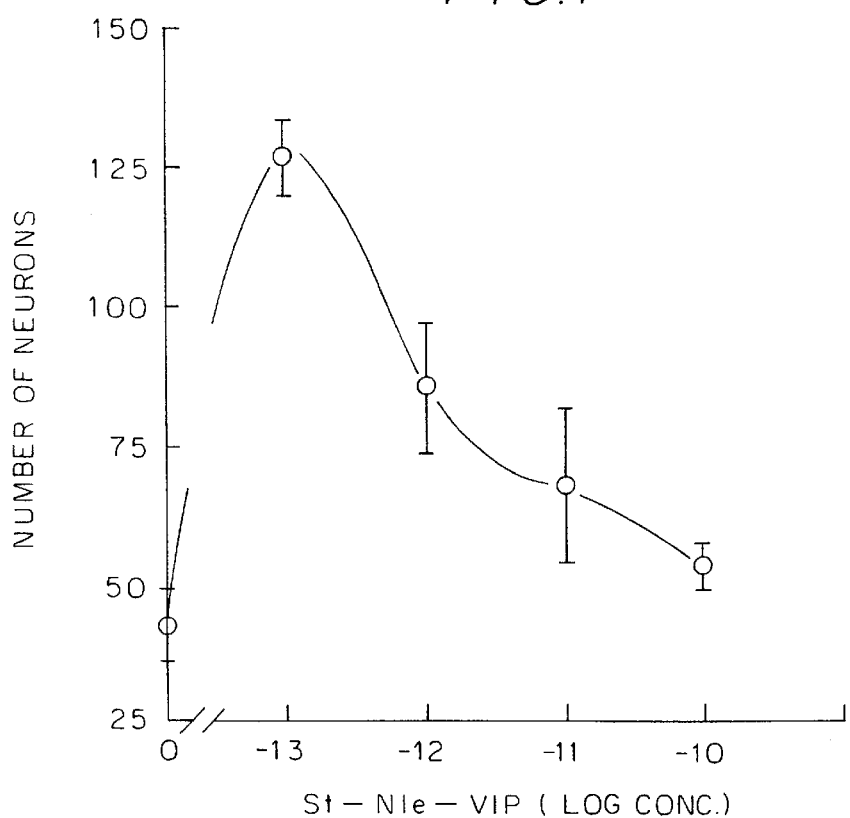
FIG. 7 shows the effect of various concentrations of St-$Nle^{17}$-VIP on the survival of neurons treated with fragment 25–35 of β-amyloid peptide.

25 μM of fragment 25–35 of β-amyloid peptide alone reduced the number of living neurons from 150 to 42 neurons per the same tested area. As can be seen in FIG. 7, St-Nle$^{17}$-VIP was able to protect neurons from the toxic effect of β-amyloid peptide fragment at all concentrations tested, the most effective protective concentrations of St-Nle$^{17}$-VIP being $10^{-13}$ M while higher concentrations showed a lower protective effect As shown previously for the short fragments, St-Nle$^{17}$-VIP protected also against naturally occurring cell death at concentrates of $10^{-10}$ and $10^{-9}$ M.

Peptide 6, shown to protect against naturally occurring cell death, also protected against β-amyloid associated death with a peak activity at $10^{-12}$ M and showing some activity above and below this concentration, e.g. at $10^{-13}$ M and $10^{-11}$ M. Protecting activity was evident even at higher concentrations (data not shown).

Figure 8:
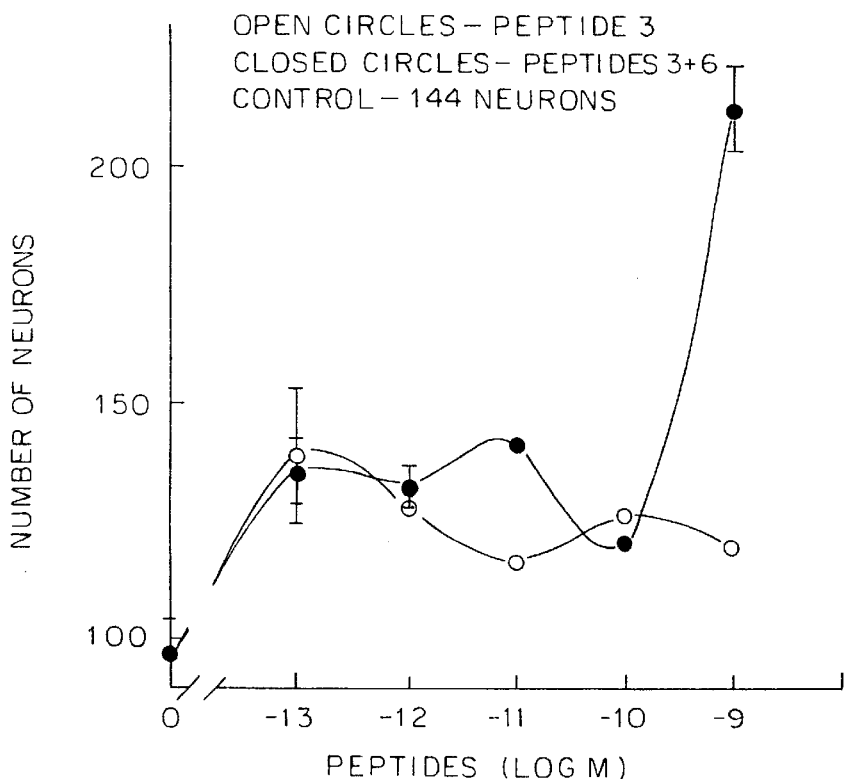
FIG. 8 shows the effect of various concentrations of peptide 3 (○) or a combination of peptide 3 and peptide 6 (●) on survival of neurons treated with fragment 25–35 of β-amyloid peptide.

As shown in FIG. 8, peptide 3 alone was also able to protect neurons from β-amyloid associated death at a wide range of concentrations. Furthermore, also a combination of peptide 3 and peptide 6 was able to protect neurons against β-amyloid associated death as well as against naturally occurring death as evident from the fact that at a concentration of $10^{-9}$ M of said combination nuerons' count was higher than that of untreated cells (144 neurons) by about 60 neurons.

These results indicate that the active agents of the invention can protect neurons from death caused by β-amyloid peptide that is involved in Alzheimer's disease neurodegencrative process.

EXAMPLE 9

Biological Test—Affinity Studies

Method (a) Cerebral cortical astrocytes were obtained and cultured as described before[16,17]. Binding studies were performed on intact cells, 5–7 days after replating at 4° C. in phosphate buffered saline containing 0.1% bovine serum albumin. Cells were divided into two groups. Group 1 was incubated with varying concentrations of St-VIP and Group 2 was incubated with varying concentrations of St-Nle$^{17}$-VIP. After 30 min. incubation with the VIP analogue, 50 pM of $^{125}$-VIP[14] was added and incubated for an hour. The media was then removed and cells were washed three times by rapid addition and removal of 1 ml phosphate buffered saline at 4° C. The labeled cells were then dissolved in 0.2 N NaOH and transferred for radioactivity counting by an automatic gamma counter (Wallac 1470 Wizard).

Figure 9A:
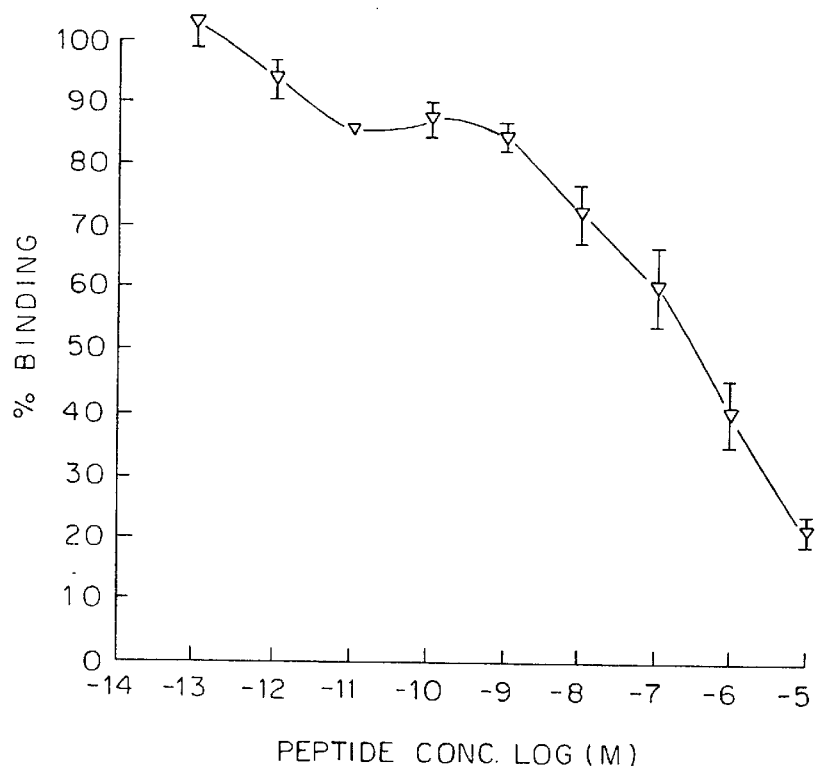
FIGS. 9 A–B show the affinity of St-$Nle^{17}$-YIP (FIG. 7A) and St-VIP (FIG. 7B) to the VIP receptor.
Figure 9B:
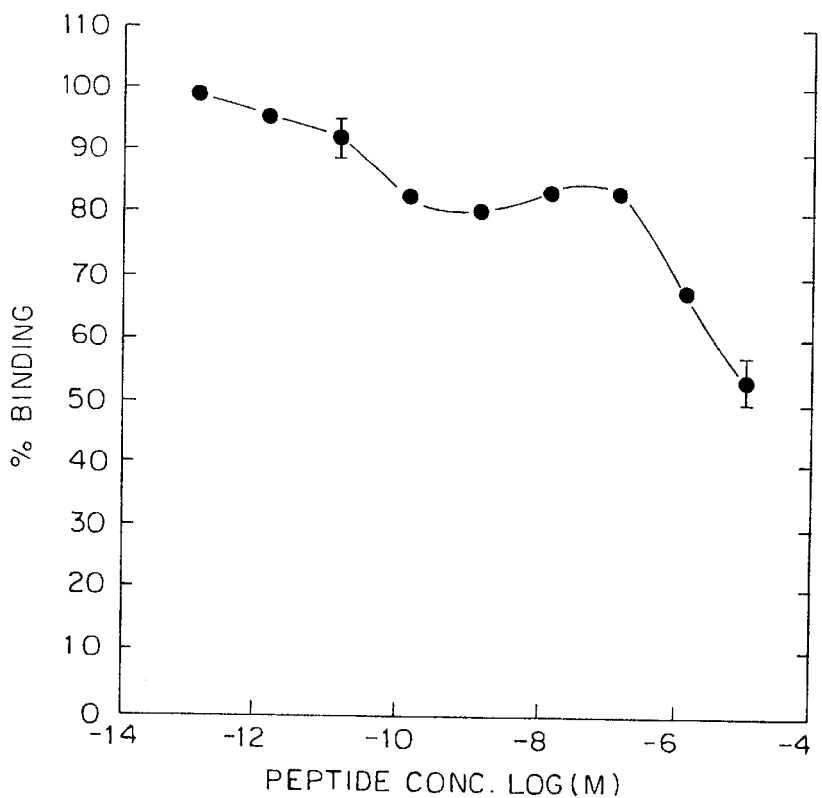

Results (b) The affinity results are shown in FIGS. 9(A) and 9(B). As can be seen at the zone of low concentration (high affinity) St-Nle$^{17}$-VIP displaced radiolabeled VIP at concentrations which were 10 fold smaller (FIG. 9(A)) than that of St-VIP (FIG. 9(B)), that is St-Nle$^{17}$-VIP has 10 fold higher affinity. At high concentration zone (low affinity zone) St-Nle$^{17}$-VIP has also a 10 fold higher affinity than St-VIP. The affinity of St-Nle$^{17}$-VIP to the high affinity receptor is about 100 fold higher than that of VIP[19].

EXAMPLE 10

Biological Test—Effects of St-Nle$^{17}$-VIP, on Learning And Memory in Animal Models of Alzheimer Method (a) Preparation of animal models of Alzheimer—I.C.V. drug administration 13 Male rats were injected intracerebroventricularly (I.C.V.) at a rate of 0.21 μl/min, using plastic tubing (PE-20) attached to 25G needle. 5 rats serving as control received an injection of saline (2 μl/side), 8 other animals received injections of ethylcholine aziridium (AF64A) (3 nmol/2 μl/side). AF64A is an inducer of cholinergic hypofunctions which mimics some of the cholinergic hypofunction reported in Alzheimer's disease and is used for preparing animal models of Alzheimer$^{(22)}$.

Animals were cannulated following injection to allow I.C.V. drug application and left to recover for a week. Learning and memory tests were conducted using the swim maze test. The 8 animals injected with AF64A were divided into two equal groups and were thereafter injected daily with either saline or 100 ng I.C.V. of St-Nle$^{17}$-VIP. The five control rats (see above) were injected with saline. Following seven injection days, behavioral assays were conducted for an additional 14 days on both control and test animals.

(b) Preparation of animal models of Alzheimer-nasal drug administration

8 Male rats were all treated with AF64A as described above. 10 days after AF64A administration 5 animals received daily nasal administration of St-Nle$^{17}$-VIP dissolved in 10% sefsol and 40% isopropanol at a concentration of 70 μg/40 μl (20 μl administered through each nostril). 3 Animals received daily nasal administration of 50 μg/40 μl of peptide 6, (20 μl/nostril) dissolved in 10% sefsol and 40% isopropanol. 6 Control animals received daily nasal administration of 10% sefsol and 40% isopropanol at an amount of 40 μl/day (20 μl nostril). The animals were partially anesthetized by diethylether prior to nasal administration. Both control and test animals were daily treated with 50,000 units of durabiotic antibiotics to avoid infection. Following 7 days of nasal administration behavioral tests were conducted on both control and test animals for an additional 8 days.

Test procedure

Test procedure was carried out according to the Morris Water Maze procedure (Morris et al, *Nature*, 297 681–683, 1982; Morris et al., *Nature*, 319, 774–776, 1986, Moser et al., *J. of Neuroci.*, 13(9), 3916–3925,1993).

Rats were placed in a circular pool, 1.26 m in diameter, 0.2 m deep, equipped with a clear plexiglas column, with a 13.3 cm platform reaching just below the surface of the water (22–24° C.). Drugs were applied daily either by injection 4 hours prior to testing or by nasal administration 1 hour prior to testing. The latency of reaching the platform was recorded for each rat (in seconds) and the changes over days of training were graphed, which reflect learning and memory.

Results (a) I.C.V. injected animals—treated with St-Nle$^{17}$-NIP

As can be seen in FIG. 10, animals injected with cholinergic blockers (□) showed a smaller improvement in the latency of reaching the platform over time, which indicated a marked decrease in learning and memory as compared to control animals (○). Animals which were injected both with cholinergic blockers and with St-Nle$^{17}$-VIP (●) showed recovery of the learning and memory abilities, essentially similar to that of control animals (○).

The above results clearly demonstrate that the agents of the invention are effective in the recovery of learning and memory ability caused by hypofunction of cholinergic neurons, which is a similar condition as appears in Alzheimer.

(b) Nasal administered animals—treated with St-Nle$^{17}$-VIP or peptide 6

Figure 11:
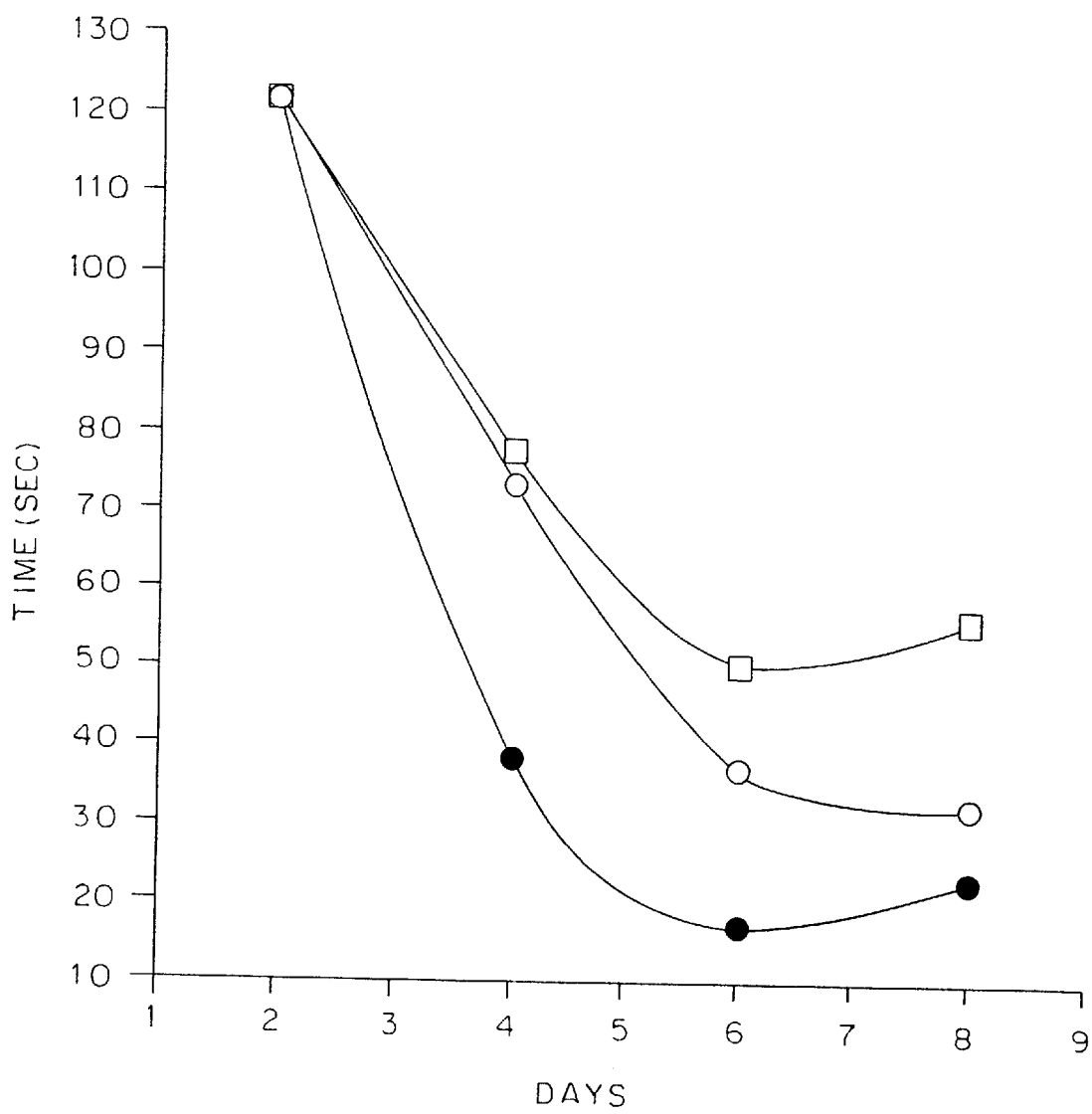
FIG. 11 shows learning and memory studies in animals injected with cholinergic blocker (□) and animals injected with cholinergic blockers and treated by nasal administration with St-$Nle^{17}$-VIP (●), or with peptide 6 (○)

As can be seen in FIG. 11, control animals (□) show smaller improvement in the latency of reaching the platform indicative of a decrease in learning and memory as compared to animals treated with both the cholinergic blocker and St-Nle$^{17}$-VIP (●) or with the cholinergic blocker and peptide 6 (○).

These results clearly indicate that the agents of the invention are also effective when administered by nasal administration.

EXAMPLE 11

Biological Test—Effects of St-Nle$^{17}$-VIP on Learning And Memory in Old Animals Method 6 Male rats aged 18–20 months were divided into hvo groups. Group 1 received daily nasal administrations of St-Nle$^{17}$-VIP dissolved in 10% sefsol at 40% isopropanol at a dose of 100 μg/40 μl/day (20 μl/nostril). Control animals were treated with daily nasal administration of 40 μl/day of 10% sefsol and 40% isopropanol (20 μl/nostril). The administration was carried out after partial anesthetization by diethylether. Animals were thus treated for 7–19 days and then were tested by placing them in a water pool as described above.

Results

Figure 12:
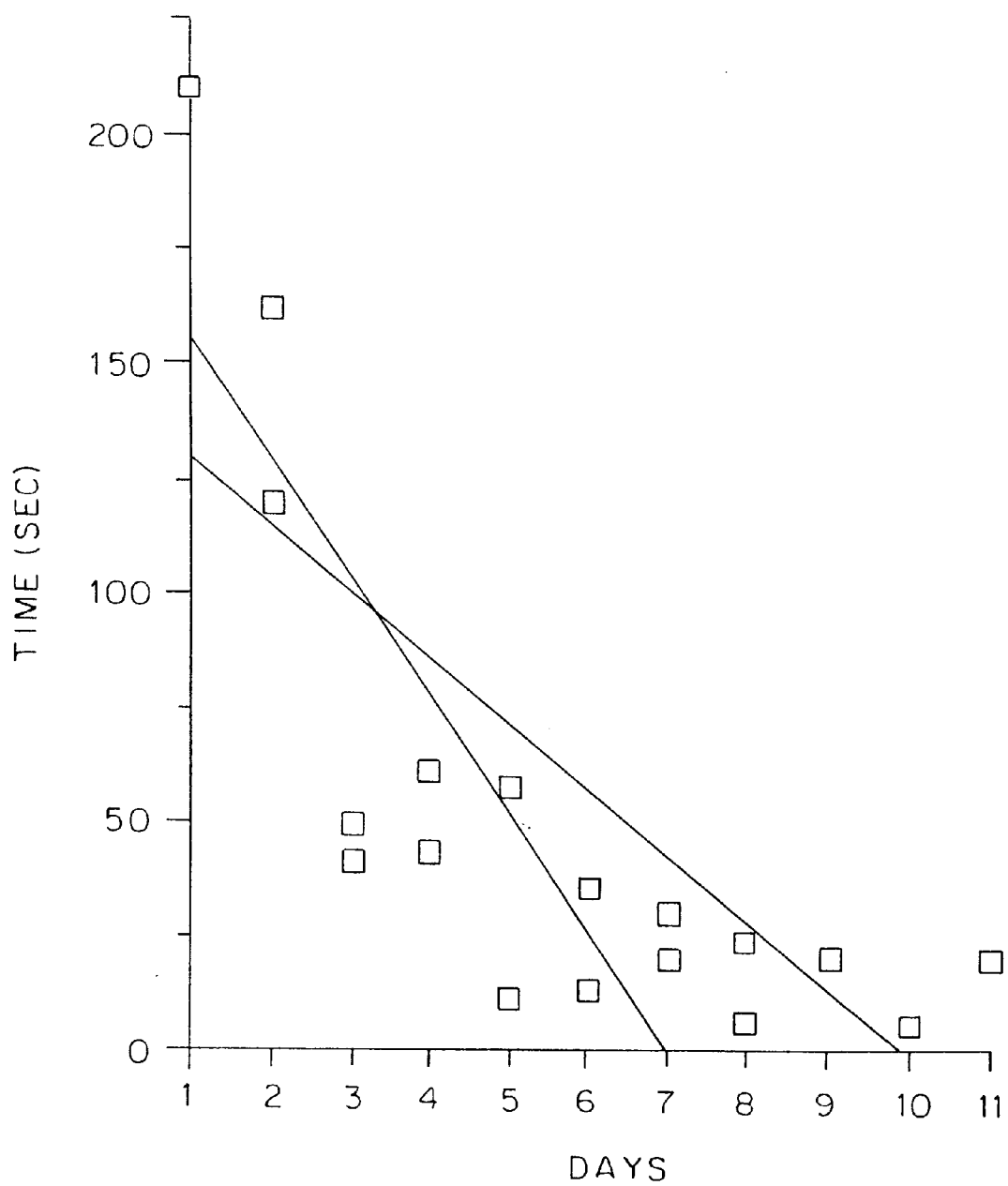
FIG. 12 shows learning and memory studies in untreated old animals (□) and old animals treated with St-$Nle^{17}$-VIP (■)

As can be seen in FIG. 12, old animals treated with St-Nle$^{17}$-VIP (■) showed a greater improvement in the latency of reaching the platform over time as compared to control untreated animals (●), indicating an increase in learning and memory capacities. These results clearly indicate that the agents of the invention are not only effective in the recovery of learning and memory ability due to pathological conditions such as Alzheimer but also due to normal physiological aging.

EXAMPLE 12

Biodistribution of St-Nle$^{17}$-VIP Following Intranasal Administration

Method

St-Nle$^{17}$-VIP was labeled with radioactive iodine and 3×10$^6$ cpn/2 μl/rat of the labeled substance were applied intranasally to 250–300 g rats. Animals were sacrificed 15 mins. following drug administration.

Radioactive tissue samples were then homogenized and subjected to centrifugation (5,400×g for 25 mins.). Supernatants were then subjected to HPLC analysis against St-Nle$^{17}$-VIP as a marker. Elution was carried out using acetonitrile gradient at fraction 30. Samples were then weighed and monitored for radioactivity in a gamma counter. To assess for the integrity of the incorporated St-Nle$^{17}$-VIP radioactive tissue, supernatants were subjected to HPLC analysis. Radioactive tissue samples were hornogenized, subjected to centrifugation and supernatnants analyzed by HPLC fractionation against St-Nle-VIP as a marker (eluting using an acetonitrile gradient at fraction 30).

Results

Figure 13:
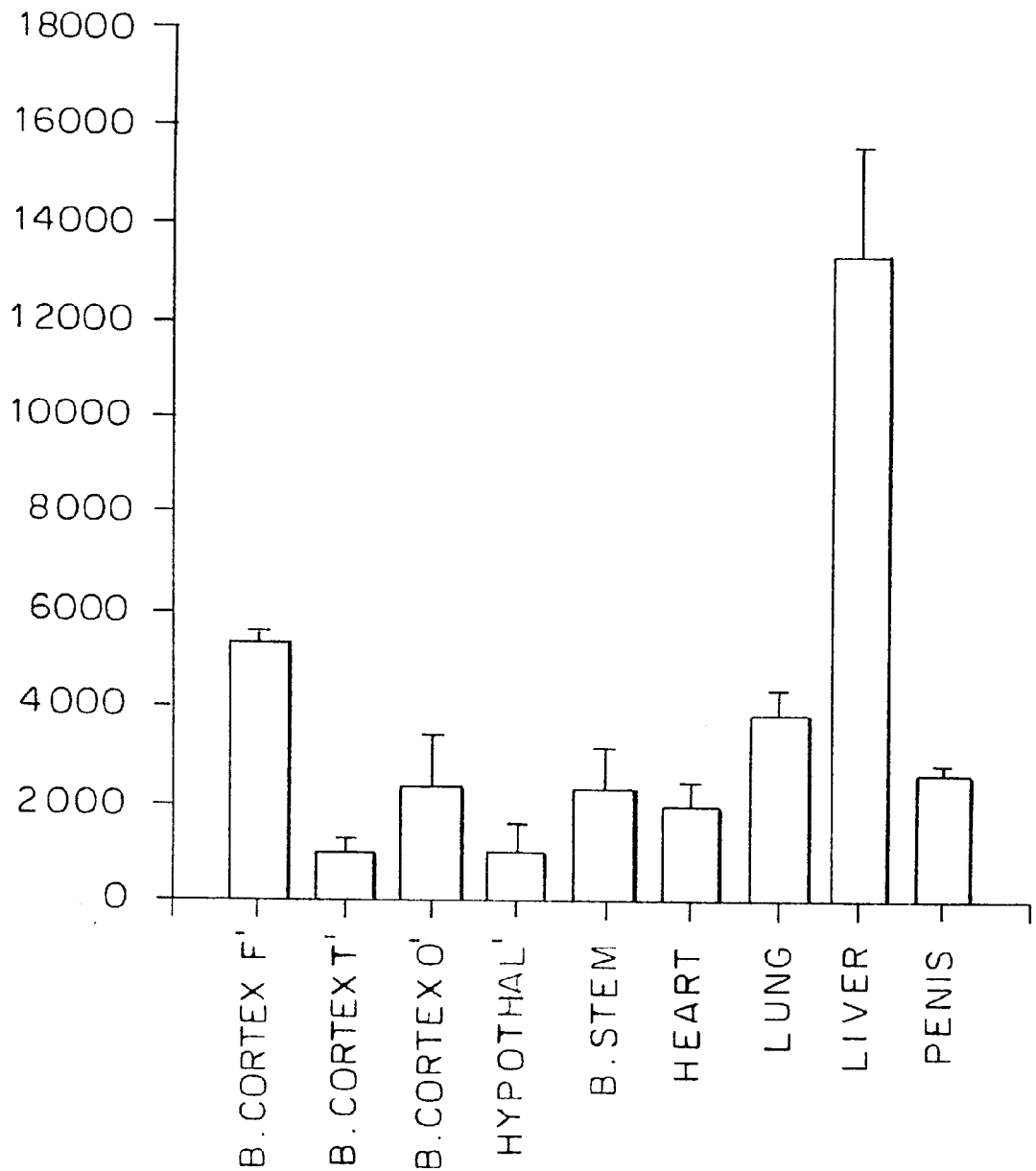
FIG. 13 shows distribution of nasally administered St-$Nle^{17}$-VIP labeled with radioactive iodine in various tissues (B=brain; F'=frontal; T'=temporal; O'=occipital)

As can be seen in FIG. 13, nasally administered St-Nle$^{17}$-VIP was able to reach the brain, and could be found in the frontal and temporal cortex, the occipital cortex, the hypothalamous—all of which are brain areas associated with cognitive facilities.

Figure 14:
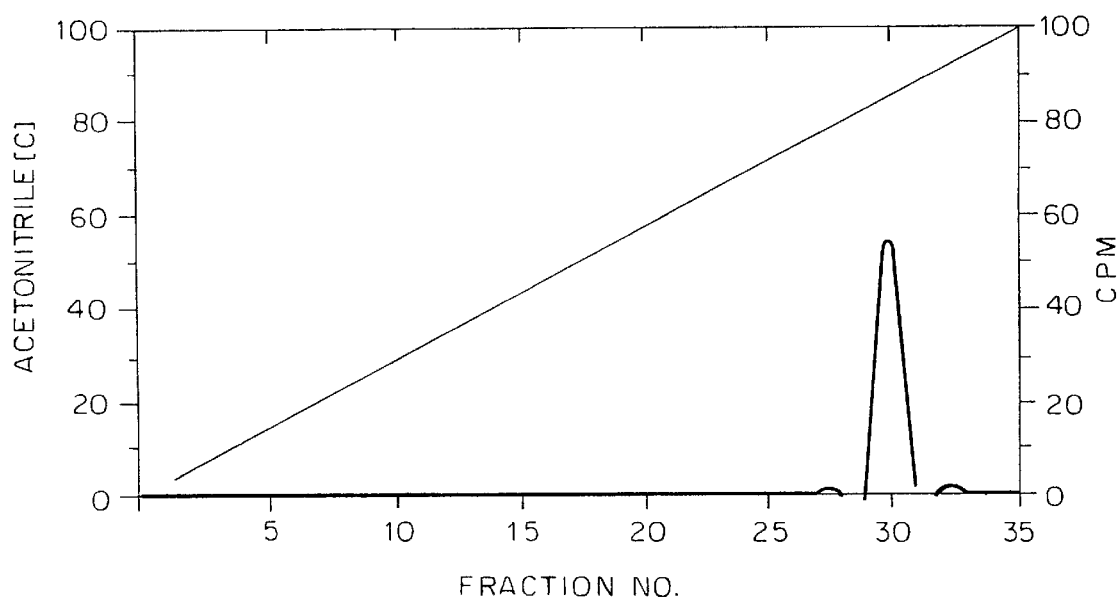
FIG. 14 shows HPLC fractionation of radioactive tissue sample supernatants against St-$Nle^{17}$-VIP as a marker.

FIG. 14 shows the radioactive peak eluting from HPLC column in fraction 30 corresponding to intact St-Nle$^{17}$-VIP. These results indicate that St-Nle$^{17}$-VIP reaches its target organs in an active, intact form.

TOXICOLOGY STUDIES

Orally Administered St-Nle$^{17}$-VIP (a) Method

The single dose toxicity of St-Nle$^{17}$-VIP administered orally was investigated in 4 groups of six male and six female rats (Sprague Dawley (S.D.) strain, purchased from Levinstein, Yokneam, Israel.)

| Test groups constitution: | | |
| --- | --- | --- |
| 1. | Saline | |
| 2. | Vehicle (sefsol + isopropanol) | |
| 3. | St-Nle$^{17}$-VIP | 7 μg/rat + vehicle |
| 4. | St-Nle$^{17}$-VIP | 7,000 μg/rat + vehicle |

Results

1. Mortality

No mortality occurred in the treatment groups at the maximum practical doso of 7000 μg/rat.

2. Side Effects

No necrotic reactions, or any other side effects were observed.

3. Body Weight Gain and Food Consumption

The rats in all groups showed normal body weight gain and showed normal food consumption during the study period. Statistical analysis (ANOVA) within the same sex revealed no significant differences. Therefore, it can be concluded that the acute medium lethal oral dose (LD$_{50}$) of St-Nle$^{17}$-VIP is greater than 7000 μg/rat which is the maximum practical dose.

Intravenously Injected St-Nle$^{17}$-VIP (b) Method

The single dose toxicity of St-Nle$^{17}$-VIP injected intravenously, in to the tail vein, was investigated in 4 groups of six male and six female rats (Sprague Dawley (S.D.) strain, purchased from Levinstein, Yokneam, Israel).

| Test group constitution: | | |
| --- | --- | --- |
| 1. | Saline | |
| 2. | Vehicle (sefsol 5% + isopropanol 50%) | |
| 3. | St-Nle$^{17}$-VIP | 7 μg/rat + vehicle |
| 4. | St-Nle$^{17}$-VIP | 7,000 μg/rat + vehicle |

Results

1. Mortality

Seven rats (3 male and 4 female out of 12) died in group 4, within 3 hours after administration. One rat died in group 2 within 5–24 hours after administration. No mortality occurred in groups 1 and 3. Under the conditions of this study, the acute intravenous median lethal dose (LD$_{50}$) of St-Nle$^{17}$VIP+vehicle was estimated to be 7,000 μg/male rat, and due to the higher mortality in females, it was estimated to be less than 7,000 μg for the combined males and females.

2. Necrotic Reaction

Necrotic reaction was observed at the site of injection (tail skin) in all groups receiving the vehicle and vehicle+drug: 55% of the animals in group 2, 58% of the animals in group 3, and all the animals in group 4.

3. Side Effects

No other side effects were observed in surviving rats of all groups.

4. Body Weight Gain and Food Consumption

Most of the surviving rats displayed normal body weight gain and showed normal food consumption during the two weeks study period. Statistical analysis (ANOVA) revealed differences between animals receiving the drug (increased weight gain) and the control group (vehicle). Following intravenous injection a weight loss was sometimes observed which was recovered later during the experiment.

Under the conditions of this study, the acute intravenous median lethal dose (LD$_{50}$) of St-Nle$^{17}$-VIP+vehicle was estimated to be 7,000 μg/male rat, and due to the higher mortality in females, it was estimated to be less than 7,000 μg for the combined males and females.

Topically Applied St-Nle$^{17}$-VIP

Method

The repeated dose toxicity of St-Nle$^{17}$-VIP administered topically was investigated in 80 SPF (specified pathogen free) rats divided into 4 groups of ten male and ten female Sprague Dawley (S.D.) strain rats purchased from Harlan, Olac, England.

| Test group constitution: | |
| --- | --- |
| Group 1: | 7 μg St-Nle$^{17}$-VIP + vehicle (1 × dose) |
| | Females: Animal numbers 1 to 10 |
| | Males: Animal numbers 41 to 50 |
| Group 2: | 700 μg St-Nle$^{17}$-VIP + vehicle (100 × dose) |
| | Females: Animal numbers 11 to 20 |
| | Males: Animal numbers 51 to 60 |
| Group 3: | 3500 μg St-Nle$^{17}$-VIP + vehicle (500 × dose) |
| | Females: Animal numbers 21 to 30 |
| | Males: Animal numbers 61 to 70 |
| Group 4: | Vehicle only (5% Sefsol + 20% isopropanol) |
| | Females: Animal numbers 31 to 40 |
| | Males: Animal numbers 71 to 80 |

Results

Mortality

No mortality associated with drug application was noted throughout the study. Only one death took place of a male from the low dose group (Group 1M, Animal number 47). Death occurred due to a massive abdominal hemorrhage caused by a nephroblastoma.

Adverse Effects

No dose related adverse effects were detected throughout the study period. Clinical signs seen were: penile oedema and erythema, yellow staining of the penis, bleeding from the preputium or vagina, abscessation in the abdominal area close to the sex organs. Most of these signs were seen transiently. One male rate developed transient diarrhea which disappeared after a week. Penile oedema, erythema and staining were seen only in the treatment groups and not in the control, however without a dose relationship.

The incidence and severity of the clinical signs were not dose related and are considered to probably be related to the repeated handling of the rats.

Body Weight Gain and Food Consumption

No significant differences were detected for either the male and female rats for body weight gain or food consumption throughout the treatment period.

Clinical Pathology

No dose related or sex related biologically meaningful treatment effects were detected for either the hematology or clinical chemistry parameters tested.

Organ Weight Analysis

No treatment related differences were noted between any of the treatment groups as compared to the control group, for either the male or female animals.

Conclusion

Under the conditions of this study, daily topical application of St-Nle$^{17}$-VIP for 13 weeks did not cause any serious adverse effects at any of the dosages tested. Minor changes which were not dose related tended to disappear despite the continuation of treatment.

Hypersensitivity Test

Skin sensitization in guinea pigs is a predictive animal test to determine the potential of substances to induce delayed hypersensitivity in humans.

A study was designed to assess the degree of skin sensitization resulting from intradermal Freund's complete adjuvant and patch application of St-Nle$^{17}$-VIP. Due to the nature of the compound and its vehicle it was decided to use the "Adjuvant and Patch Test".

The logic of the dose design was as follows: pharmacological experimentation has shown that the biologically active dose is 7 μg per rat. The dose of 1000× the biologically active dose was chosen for this experiment.

Method

| Test Material | |
|---|---|
| Name | St-Nle$^{17}$-VIP (prepared and purified as described in Example 1) |
| Appearance | Powder |
| Stability | Powder (for a year) Refrigerated in a solubilized form (for at least six weeks) |
| Vehicle | Sefsol (purchased from Sigma Co.) + Isopropanol |

Preparation of test material+vehicle per animal 7 mg St-Nle$^{17}$-VIP+250 μl 10% Sefsol+250 μl 40% isopropanol [500 μl/animals=1000×dose].

The material was mixed on the same day, 3 hours before dosing.

Positive control substance

1% 1-chloro-2,4-dinitrobenzene in dibutylphthalate.

Results

Both St-Nle$^{17}$-VIP dissolved in vehicle and the vehicle alone did not cause a hypersensitivity response, while positive control application of 1-chloro-2,4-dinitrobenzenie caused prominent hypersensitivity reaction in guinea pigs.

This study showed that both St-Nle$^{17}$-VIP and the vehicle alone have no skin sensitization properties.

Mutagenic Activity

St-Nle$^{17}$-VIP was examined for mutagenic activity in five histidine-dependent auxotrophs of *Salmonella typhimurium* strains TA-1535, TA-100, TA-1538, TA-98 and TA-1537, using pour-plate assays. The procedures used complied with the OECD Guidelines 471, adopted May 1983 and EPA Guidelines CFR 40, Part 798.5265.

The studies, which were conducted in the absence and presence of an activating system derived from rat liver (S-9 mix), employed a range of levels selected following a preliminary toxicity test in strain TA-98. Each test was conducted in triplicate and was carried out on two separate occasions. Positive controls such as known mutagens: sodium azide, 4-nitro-o-phenylenediamine (NPD), ICR-191 and 2-aminoanthracene,were used under the same experimental conditions.

No significant increases in revertant colony numbers over control counts were obtained with any of the tester strains following exposure to the test material at levels from 0.3 to 312.5 μg per plate, either in the presence or the absence of the S-9 mix.

Under the conditions of this study the test material St-Nle$^{17}$-VIP is devoid of mutagenic activity.

LIST OF REFERENCES

1. Gozes, I. and Brenneman, D. E. (1989) *Molecular Neurobiology,* 3, 201–236.
2. Gozes, I., Hill, J. M., Mervis, R. F., Fridkin, M. and Brenneman, D. E. (1990) *Soc. Neurosci. Abs.* 16, 1292.
3. Hill, J. M., Gozes, I., Hill, J. L., Fridkin, M. and Brenneman, D. E. (1991) *Peptides* 12, 187–192.
4. Glowa, J. R., Panlilio, L. V., Brenneman, D. E., Gozes, I., Fridkin, M., Hill, J. M. (1992) *Brain Res.* 570, 49–53.
5. Rossor, M. et al., (1980) *Brain Res.,* 201, 249–253.
6. Bouras, C., de St. Hilare-Kafi, K. and Constantinidis, J. (1986) *Frog. Neurophychophamacol. Biol. Psychiatry* 10, 271–286.
7. Sunderland, T. et al., (1991), *Biol. Psychiatry,* 30(1), 81–87.
8. Sunderland, T. et al., (1991), *Biol. Psychiatry,* 30, 83–87.
9. Wikkelsö et al., (1991), *Eur. Neurol,* 31, 88–93.
10. Arai, H., Moroji, T. and Koska, K. (1984) *Neurosci Let.* 52, 73–78.
11. Merrfield, R. B. (1963) *J. Am. Chem. Soc* 85, 2149.
12. Steuart J. M. and Young, J. D., (1984) *Solide Phase Peptide Synthesis,* Pierce Chemical Corp., Rockford, Ill., (2nd edition).
13. Sakakibara, S. et al., (1967) *Bull. Chem. Soc. Japan* 40, 2164.
14. Werner, H. et al., (1988) *Biochem. Biophys. Res. Commun.* 133, 288.
15. Brenneman D. E., Neale, E. A., Foster, G. A., d'Autremont, S., Westbrook, G. L. (1987) *J. Cell Biology* 104, 1603–1610.
16. McCarthy, K. D. and de Vellis, J. (1980) *J. Cell Biol.* 85, 890–902.
17. Evans, T., McCarthy, K. D., Harden, T. K. (1984) *J. Neurochem.* 43, 131–138.
18. Gozes, I., Meltzor, E. Rubinrout, S., Brenneman, D. E. and Fridkin, M. (1989) *Endocrinology* 125, 2945–2949.
19. Gozes, I., McCune, S. K., Jacobson, L., Warren, D., Moody, T. W., Fridkin, M., Brenneman, D. E. (1991) *J. Pharmacol. Experm. Therap.* 257, 959–966.
20. Gozes, Y., Brenneman, D. E., Fridkin, M., Asofsky, R., Gozes, L (1991) *Brain Res.* 540, 319–321.
21. Tate, B. A., M. K., Lee and C. A. Marotta (1992) *Soc. Neurosci. Abs.* 18, 197.
22. Fisher, A. et al., (1989), *Neurosci. Letters,* 102, 325–331.

We claim:

1. A method for the protection of neurons against neuronal cell death, comprising administering to a patient in need of neuronal protection a therapeutically effective amount of a conjugate of a lipophilic moiety and a peptide having the formula:

<u>His</u>-Ser-Asp-Ala-X$^1$-(Phe or Thr)-Thr-Asp-Asn-Tyr-

Thr-Arg-Leu-Arg-Lys-Gln-X$^2$-Ala-X$^3$-Lys-Lys-Tyr-Leu- (Asn or Ala)-(Ser or Ala)-(Ile or Val)-Leu-Asn, wherein $X^1$, $X^2$ and $X^3$ may be the same or different and each is a residue of a natural or non-natural lipophilic amino acid (SEQ ID NO:8),
or a physiologically active fragment of said peptide, wherein said conjugate has a neuroprotecting effect which is better than that of VIP, said conjugate being optionally in combination with a pharmaceutically acceptable carrier.

2. A method according to claim 1, wherein said conjugate is selected from the group consisting of:
   (i) Stearoyl-VIP;
   (ii) Stearoyl-norleucine$^{17}$-VIP;
   (iii) Stearoyl-Ala-Val-Lys-Lys-Tyr-Leu-Asn-Ser-Ile-Leu-Asn-NH$_2$ (SEQ ID NO:3);
   (iv) Stearoyl-Ala-Val-Thr-Thr-Asp-Asn-Tyr-Thr-NH$_2$ (SEQ ID NO:4);
   (v) Stearoyl-His-Ser-Asp-Ala-Val-Phe-Thr-Asp-Asn-Tyr-Thr-Arg-Leu-Arg-NH$_2$ (SEQ ID NO:5); and
   (vi) Stearoyl-Lys-Gln-Met-Ala-Val-Lys-Lys-Tyr-Leu-Ala-Ala-Val-Leu-NH$_2$ (SEQ ID NO:6).

3. A method according to claim 1, wherein said patient in need of neuronal protection is one suffering from dementia.

4. A method according to claim 1, wherein said patient in need of neuronal protection is one suffering from Alzheimer caused dementia.

5. A method according to claim 1, wherein said patient in need of neuronal protection is one suffering from age caused dementia.

6. A method according to claim 1, wherein the peptide is nasally administered.

7. A method in accordance with claim 1, wherein said peptide is selected from the group consisting of:
   (i) vasoactive intestinal peptide (VIP);
   (ii) norleucine $^{17}$-VIP;
   (iii) Ala-Val-Lys-Lys-Tyr-Leu-Asn-Ser-Ile-Leu-Asn-NH$_2$ (SEQ ID NO:3);
   (iv) Ala-Val-Thr-Thr-Asp-Asn-Tyr-Thr-NH$_2$ (SEQ ID NO:4);
   (v) His-Ser-Asp-Ala-Val-Phe-Thr-Asp-Asn-Tyr-Thr-Arg-Leu-Arg-NH$_2$ (SEQ ID NO:5);
   (vi) Lys-Gln-Met-Ala-Val-Lys-Lys-Tyr-Leu-Ala-Ala-Val-Leu-NH$_2$ (SEQ ID NO:6); and
   (vii) a physiologically active fragment of (i)–(vi).

8. A method according to claim 1 wherein $X^1$, $X^2$ and $X^3$ are the same or different and each is selected from the group consisting of leucine, isoleucine, norleucine, valine, tryptophan, phenylalanine, methionine, octahydroindole-2-carboxylic acid (oic), cyclohexylglycine (chg) and cyclopentylglycine (cpg).

9. A method in accordance with claim 1 wherein said lipophilic moiety is stearoyl, lauroyl or caproyl.

* * * * *